(12) United States Patent
Ishihara

(10) Patent No.: US 9,182,347 B2
(45) Date of Patent: Nov. 10, 2015

(54) FLUOROSCOPY APPARATUS, FLUOROSCOPY SYSTEM, AND FLUORESCENCE-IMAGE PROCESSING METHOD

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 59 days.

(21) Appl. No.: 14/173,202

(22) Filed: Feb. 5, 2014

(65) Prior Publication Data
US 2014/0161369 A1 Jun. 12, 2014

Related U.S. Application Data

(63) Continuation of application No. PCT/JP2012/070241, filed on Aug. 8, 2012.

(30) Foreign Application Priority Data

Aug. 18, 2011 (JP) ................................. 2011-178922

(51) Int. Cl.
*G06K 9/40* (2006.01)
*G01N 21/64* (2006.01)
(Continued)

(52) U.S. Cl.
CPC ............ *G01N 21/64* (2013.01); *A61B 1/00009* (2013.01); *A61B 1/043* (2013.01); *A61B 1/0638* (2013.01); *A61B 1/0646* (2013.01); *G02B 23/2461* (2013.01); *G06T 5/009* (2013.01)

(58) Field of Classification Search
None
See application file for complete search history.

(56) References Cited

U.S. PATENT DOCUMENTS 6,516,217 B1    2/2003   Tsujita
8,129,105 B2 *  3/2012   Zuckerman .................. 435/4
(Continued)

FOREIGN PATENT DOCUMENTS

CN    1367455 A      9/2002
EP    2 314 198 A1   4/2011
(Continued)

OTHER PUBLICATIONS

International Search Report dated Oct. 30, 2012 issued in PCT/JP2012/070241.
(Continued)

*Primary Examiner* — Phuoc Tran
(74) *Attorney, Agent, or Firm* — Scully, Scott, Murphy & Presser, PC

(57) ABSTRACT

A fluoroscopy apparatus includes a preprocessing section that multiplies at least one of a fluorescence image and a reference-light image by a coefficient by which distance characteristics of fluorescence intensity and distance characteristics of return-light intensity acquired from a standard sample in advance are made directly proportional to each other to generate a correction fluorescence image and a correction reference-light image; a divided-image generating section that divides the correction fluorescence image by the correction reference-light image to generate a divided image; a threshold-setting section that sets a threshold based on a mean grayscale level of pixels in the divided image; an image-adjusting section that enhances contrast between a region with grayscale levels above the set threshold set by the threshold-setting section and a region with grayscale levels below the threshold in the divided image; and a monitor that displays the divided image with the enhanced contrast.

20 Claims, 13 Drawing Sheets

(51) Int. Cl.
*A61B 1/04* (2006.01)
*A61B 1/06* (2006.01)
*G02B 23/24* (2006.01)
*A61B 1/00* (2006.01)
*G06T 5/00* (2006.01)

(56) References Cited

U.S. PATENT DOCUMENTS

2001/0056238 A1* 12/2001 Tsujita ............................ 600/476
2002/0168096 A1* 11/2002 Hakamata et al. ............. 382/132
2003/0218137 A1* 11/2003 Sendai ........................ 250/461.1
2004/0064016 A1  4/2004 Kobayashi et al.
2011/0085713 A1  4/2011 Yan et al.

FOREIGN PATENT DOCUMENTS

| | | | |
|---|---|---|---|
| JP | 62-247232 | A | 10/1987 |
| JP | 3-58729 | B2 | 9/1991 |
| JP | 2001-017379 | A | 1/2001 |
| JP | 2003-036436 | A | 2/2003 |
| JP | 2003-164414 | A | 6/2003 |
| JP | 2006-175052 | A | 7/2006 |
| JP | 2010-220894 | A | 10/2010 |
| JP | 2011-087929 | A | 5/2011 |
| WO | WO 2010/110138 | A1 | 9/2010 |
| WO | WO 2011/099363 | A1 | 8/2011 |
| WO | WO 2011/111619 | A1 | 9/2011 |
| WO | WO 2011/115095 | A1 | 9/2011 |

OTHER PUBLICATIONS

Extended Supplementary European Search Report dated Apr. 24, 2015 from related European Application No. 12 82 3651.0.

Chinese Office Action dated May 28, 2015 from related Chinese Patent Application No. 201280039584.2.

* cited by examiner

FIG. 2

| EXAMINATION DISTANCE | 200 | ... | 120 | ... | 25 | ... | 10 |
|---|---|---|---|---|---|---|---|
| RETURN-LIGHT IMAGE | 331 | ... | 294 | ... | 4617 | ... | 14000 |
| FLUORESCENCE IMAGE | 5031 | ... | 5893 | ... | 53126 | ... | 27000 |
| RETURN-LIGHT GAIN | 1 | ... | 1 | ... | 1 | ... | 1 |
| FLUORESCENCE GAIN | 150 | ... | 150 | ... | 100 | ... | 30 |
| RETURN-LIGHT EXPOSURE TIME | 20 | ... | 15 | ... | 10 | ... | 7 |
| FLUORESCENCE EXPOSURE TIME | 100 | ... | 100 | ... | 70 | ... | 30 |
| NORMALIZED RETURN-LIGHT IMAGE | 16.6 | ... | 37.5 | ... | 461.7 | ... | 2000 |
| NORMALIZED FLUORESCENCE IMAGE | 33.5 | ... | 72.2 | ... | 758.9 | ... | 3000 |
| FLUORESCENCE/ RETURN LIGHT | 2.024 | ... | 1.923 | ... | 1.644 | ... | 1.500 |

FIG. 3

| NORMALIZED RETURN-LIGHT IMAGE | 16.6 | ... | 37.5 | ... | 461.7 | ... | 2000 |
|---|---|---|---|---|---|---|---|
| COEFFICIENT | 2.024 | ... | 1.923 | ... | 1.644 | ... | 1.500 |

FLUOROSCOPY APPARATUS, FLUOROSCOPY SYSTEM, AND FLUORESCENCE-IMAGE PROCESSING METHOD

CROSS-REFERENCE TO RELATED APPLICATIONS

This is a continuation of International Application PCT/JP2012/070241, with an international filing date of Aug. 8, 2012, which is hereby incorporated by reference herein in its entirety. This application is based on Japanese Patent Application No. 2011-178922, the contents of which are incorporated herein by reference.

TECHNICAL FIELD

The present invention relates to fluoroscopy apparatuses, fluoroscopy systems including such fluoroscopy apparatuses, and fluorescence-image processing methods.

BACKGROUND ART

There are known methods for correcting for variations in the brightness of a fluorescence image with examination distance and angle by dividing the fluorescence image by a reflected-light image (see, for example, PTLs (Patent Literatures) 1 to 3).

CITATION LIST

Patent Literature

{PTL 1}
Japanese Unexamined Patent Application, Publication No.
{PTL 2}
Japanese Examined Patent Application, Publication No. 3-58729
{PTL 3}
Japanese Unexamined Patent Application, Publication No. 2006-175052

SUMMARY OF INVENTION

An aspect of the present invention is a fluoroscopy apparatus including a light source that irradiates a subject with excitation light and reference light; a fluorescence-image acquiring section that captures fluorescence emitted from the subject irradiated with the excitation light from the light source to acquire a fluorescence image; a reference-light-image acquiring section that captures return light returning from the subject irradiated with the reference light from the light source to acquire a reference-light image; a preprocessing section that multiplies at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image; a divided-image generating section that divides the correction fluorescence image generated by the preprocessing section by the correction reference-light image to generate a divided image; a threshold-setting section that sets a threshold based on a mean grayscale level of pixels in the divided image generated by the divided-image generating section; an image-adjusting section that enhances contrast between a region with grayscale levels above the threshold set by the threshold-setting section and a region with grayscale levels below the threshold in the divided image; and a display that displays the divided image with the contrast enhanced by the image-adjusting section.

Another aspect of the present invention is a fluoroscopy apparatus including a light source that irradiates a subject with excitation light and reference light; a fluorescence-image acquiring section that captures fluorescence emitted from the subject irradiated with the excitation light from the light source to acquire a fluorescence image; a reference-light-image acquiring section that captures return light returning from the subject irradiated with the reference light from the light source to acquire a reference-light image; a preprocessing section that multiplies at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image; a divided-image generating section that divides the correction fluorescence image generated by the preprocessing section by the correction reference-light image to generate a divided image; a threshold-setting section that sets a threshold based on a mean grayscale level of pixels in the divided image generated by the divided-image generating section; an image-adjusting section that enhances contrast between a region with grayscale levels above the threshold set by the threshold-setting section and a region with grayscale levels below the threshold in the divided image; and a display that displays the divided image with the contrast enhanced by the image-adjusting section.

Another aspect of the present invention is a fluorescence-image processing method using a fluorescence image acquired by capturing fluorescence emitted from a subject when the subject is irradiated with excitation light and a reference-light image acquired by capturing return light returning from the subject when the subject is irradiated with reference light. The method includes a preprocessing step of multiplying at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image; a divided-image generating step of dividing the correction fluorescence image generated by the preprocessing step by the correction reference-light image to generate a divided image; a threshold-setting step of setting a threshold based on a mean grayscale level of pixels in the divided image generated by the divided-image generating step; an image-adjusting step of enhancing contrast between a region with grayscale levels above the threshold set by the threshold-setting step and a region with grayscale levels below the threshold in the divided image; and a display step of displaying the divided image with the contrast enhanced by the image-adjusting step.

Another aspect of the present invention is a fluorescence-image processing method using a fluorescence image acquired by capturing fluorescence emitted from a subject when the subject is irradiated with excitation light and a reference-light image acquired by capturing return light returning from the subject when the subject is irradiated with reference light. The method includes a preprocessing step of multiplying at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image; a divided-image generating step of dividing the correction fluorescence image generated by the preprocessing step by the correction reference-light image to generate a divided image; a threshold-setting step of setting a threshold based on a mean grayscale level of pixels in the divided image generated by the divided-image generating step; an image-adjusting step of enhancing contrast between a region with grayscale levels above the threshold set by the threshold-setting step and a region with grayscale levels below the threshold in the divided image; and a display step of displaying the divided image with the contrast enhanced by the image-adjusting step.

BRIEF DESCRIPTION OF DRAWINGS

FIG. 2 is a diagram showing an example of a list of correspondences between the grayscale levels, gains, and exposure times of images and normalized images for deriving coefficients used in the fluoroscopy apparatus in FIG. 1 and the coefficients derived therefrom.

FIG. 3 is a diagram showing an example of a list of correspondences between the grayscale levels of the normalized reference-light images and the coefficients derived in FIG. 2.

DESCRIPTION OF EMBODIMENTS

First Embodiment

A fluoroscopy apparatus according to a first embodiment of the present invention will be described below with reference to the drawings.

Figure 1:
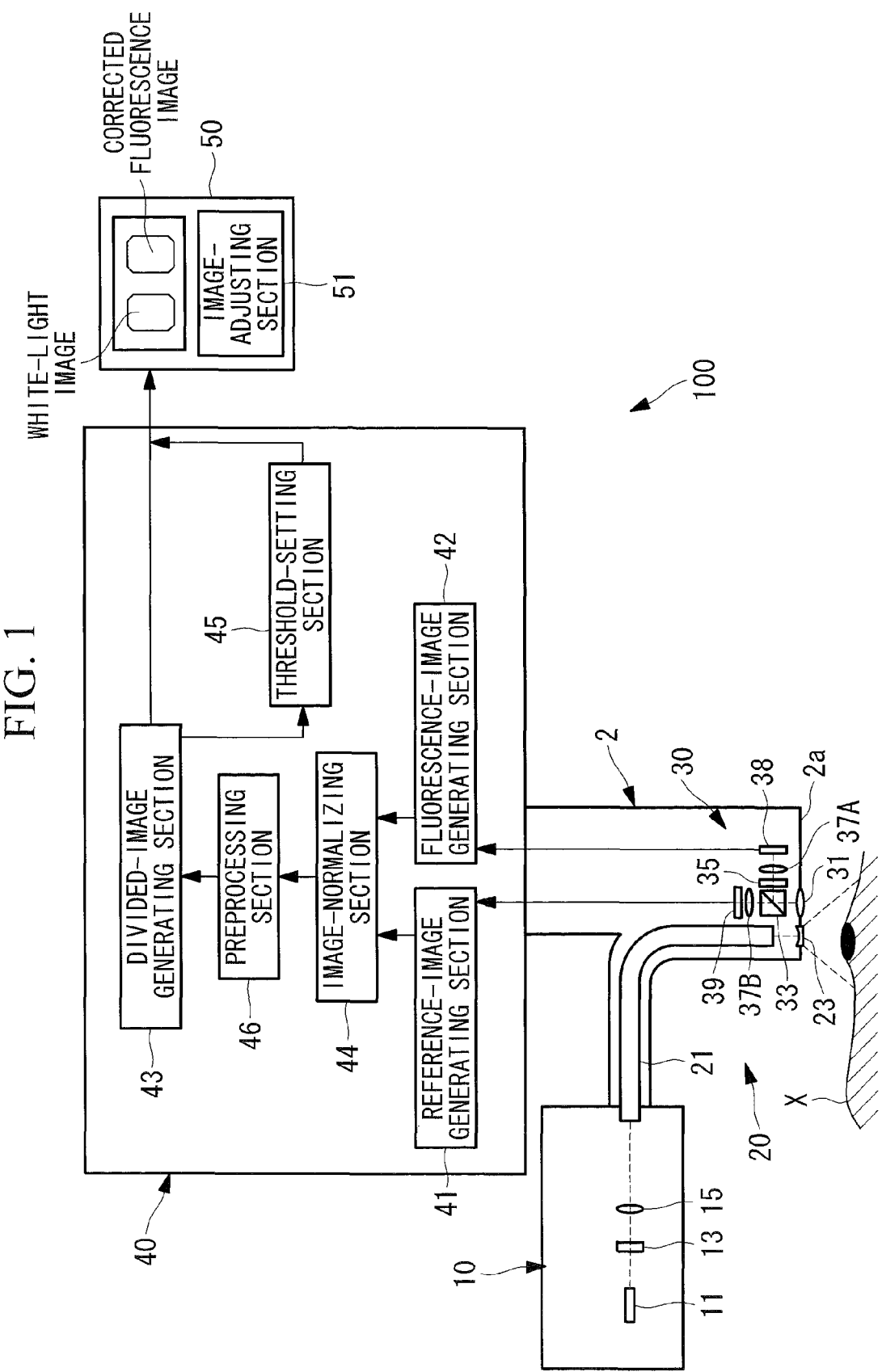
FIG. 1 is a schematic block diagram of a fluoroscopy apparatus according to a first embodiment of the present invention.

As shown in FIG. 1, a fluoroscopy apparatus 100 according to this embodiment includes a long, thin scope 2 that is inserted into a body cavity; an illumination unit 20 including a light source 10 that emits illumination light to be output from a distal end 2a of the scope 2; an image-capturing unit 30 that is disposed in the scope 2 and that acquires image information from the subject, i.e., an examination target site X; an image processor 40 that processes the image information acquired by the image-capturing unit 30; and a monitor (display) 50 that displays, for example, the image and image information processed by the image processor 40.

The light source 10 includes a xenon lamp (Xe lamp) 11 that emits illumination light, an excitation-light filter 13 that extracts excitation light and white light (reference light) from the illumination light emitted from the xenon lamp 11, and a coupling lens 15 that converges the white light containing the excitation light extracted by the excitation-light filter 13. The excitation-light filter 13 extracts, for example, white light containing excitation light in the wavelength range of 400 to 740 nm.

The illumination unit 20 includes a light-guide fiber 21 disposed over substantially the entire length of the scope 2 in the longitudinal direction thereof and a spreading lens 23 disposed at the distal end 2a of the scope 2.

The light-guide fiber 21 guides the white light containing the excitation light condensed by the coupling lens 15 to the distal end 2a of the scope 2. The spreading lens 23 causes the white light containing the excitation light guided by the light-guide fiber 21 to be spread out onto the examination target site X.

The image-capturing unit 30 includes an objective lens 31 that collects return light returning from the examination target site X irradiated with the white light containing the excitation light by the illumination unit 20 and a beam splitter 33 that splits the return light collected by the objective lens 31 into different wavelengths.

The objective lens 31 is disposed beside the spreading lens 23 at the distal end 2a of the scope 2. Of the return light, the beam splitter 33 reflects light (excitation light and fluorescence) with wavelengths longer than or equal to the examination wavelength and transmits white light (return light) with wavelengths shorter than the excitation wavelength.

The image-capturing unit 30 includes an excitation-light cut filter 35 that, of the excitation light and fluorescence reflected by the beam splitter 33, blocks the excitation light and transmits only the fluorescence (e.g., near-infrared fluorescence); a focusing lens 37A that focuses the fluorescence transmitted by the excitation-light cut filter 35; a focusing lens 37B that focuses the white light transmitted by the beam splitter 33; a fluorescence-image capturing section 38 that captures the fluorescence focused by the focusing lens 37A; and a white-light-image capturing section 39 that captures the white light focused by the focusing lens 37B.

The excitation-light-cut filter 35 transmits, for example, only fluorescence in the wavelength range of 765 to 850 nm. The fluorescence-image capturing section 38 is, for example, a high-sensitivity monochrome CCD sensor for fluorescence.

The fluorescence-image capturing section 38 captures the fluorescence, thereby acquiring fluorescence image information. The white-light-image capturing section 39 is, for example, a color CCD sensor for white light, including a mosaic filter (not shown). The white-light-image capturing section 39 captures the white light, thereby acquiring white-light image information.

The image processor 40 includes a reference-image generating section 41 that generates a white-light image (reference-light image) from the white-light image information acquired by the white-light-image capturing section 39; a fluorescence-image generating section 42 that generates a fluorescence image from the fluorescence image information acquired by the fluorescence-image capturing section 38; and an image-normalizing section 44 that normalizes the reference-light image generated by the reference-image generating section 41 and the fluorescence image generated by the fluorescence-image generating section 42 to generate a normalized reference-light image and a normalized fluorescence image.

The image processor 40 also includes a preprocessing section 46 that generates a correction reference-light image from the normalized reference-light image generated by the image-normalizing section 44 and a correction fluorescence image from the normalized fluorescence image generated by the image-normalizing section 44; a divided-image generating section 43 that divides the correction fluorescence image generated by the preprocessing section 46 by the correction reference-light image to generate a divided image (hereinafter also referred to as "corrected fluorescence image"); and a threshold-setting section 45 that sets a threshold for the grayscale levels in the divided image generated by the divided-image generating section 43.

The reference-image generating section 41 generates a two-dimensional white-light image from the white-light image information acquired by the white-light-image capturing section 39.

The fluorescence-image generating section 42 generates a two-dimensional fluorescence image from the fluorescence image information acquired by the fluorescence-image capturing section 38.

The fluorescence image may be, for example, an image of fluorescence from the fluorescent dye Cy7. In particular, a tumor-specific fluorescence image can be acquired if a tumor-specific fluorescent chemical, such as a fluorescent chemical made of Cy7 bound to an antibody against the cancer-specific molecule CEA (anti-CEA antibody), is administered in advance to the examination target. The reference-light image may be, for example, an image based on the illumination light reflected back from the surface of the examination target and the illumination light scattered back from inside the examination target.

The image-normalizing section 44 normalizes the reference-light image and the fluorescence image using the relational equation represented by Eq. 1.

$$\text{normalized grayscale level} = \frac{\text{grayscale level of acquired image}}{\text{exposure time}} \times \frac{\text{predetermined gain}}{\text{examination gain}} \quad \{\text{Eq. 1}\}$$

Specifically, when the white-light-image capturing section 39 and the fluorescence-image capturing section 38 acquire the reference-light image and the fluorescence image as 16-bit grayscale images, the exposure time and the gain are adjusted so that the grayscale level of each pixel falls within the above range; therefore, normalization is executed to maintain constant examination conditions. In Eq. 1, the predetermined gain is, for example, set to 1 in white-light examination and set to 100 in fluorescence examination.

The preprocessing section 46 includes a storage section (not shown) that stores a coefficient by which the distance characteristics of fluorescence intensity for a standard sample and the distance characteristics of return-light intensity for the same standard sample are made directly proportional to each other in association with the return-light intensity, and reads the coefficient corresponding to the grayscale level of each pixel in the input reference-light image from the storage section and multiplies the grayscale level by the coefficient to generate a correction reference-light image. In this case, the preprocessing section 46 outputs the input fluorescence image directly as a correction fluorescence image.

FIGS. 2 and 3 show examples of coefficients calculated based on the grayscale levels of a reference-light image and a fluorescence image acquired when a phantom or an organ such as a swine organ is examined as a standard sample, with the examination distance varying, for example, from 10 to 200 mm.

Specifically, if the grayscale level (return-light intensity) of one pixel in the acquired reference-light image is 16.6, the grayscale level of that pixel is multiplied by the coefficient 2.024. This is repeated for all pixels to generate a correction reference-light image. If the grayscale level of any pixel is between two grayscale levels shown in FIG. 3, the grayscale level of that pixel is multiplied by a coefficient given by linear interpolation between the two coefficients corresponding to the grayscale levels in FIG. 2.

The divided-image generating section 43 divides the correction fluorescence image generated by the preprocessing section 46, as described above, by the correction reference-light image to generate a divided image. Thus, a divided image with reduced variations in the fluorescence intensity of the fluorescence image depending on factors such as examination distance is generated. The divided-image generating section 43 also outputs the white-light image and the resulting divided image (corrected fluorescence image) on the monitor 50.

The threshold-setting section 45 sets, as a threshold, the mean grayscale level m of the individual pixels in the divided image (the mean grayscale level of the entire image) multiplied by a predetermined coefficient a, as shown in calculation formula (1) below.

{Eq. 2}

$$S = a \times m \quad (1)$$

The monitor 50 can simultaneously display the white-light image and the divided image (corrected fluorescence image) fed from the divided-image generating section 43. The monitor 50 also includes an image-adjusting section 51 that adjusts the grayscale levels in the divided image.

The image-adjusting section 51 replaces pixels with grayscale levels below the threshold S by a grayscale level of 0 for enhanced contrast between a pixel region with grayscale levels above the threshold S set by the threshold-setting section 45 and a pixel region with grayscale levels below the threshold S in the divided image.

The operation of the thus-configured fluoroscopy apparatus 100 according to this embodiment will now be described.

To examine an examination target site X in a body cavity of a living body using the fluoroscopy apparatus 100 according to this embodiment, a fluorescent chemical that preferentially accumulates in an affected area, such as cancer cells, is deposited on or absorbed into the examination target site X. When the examination target site X in this state is irradiated with excitation light, the fluorescent chemical is excited, emitting fluorescence. Because, in practice, the fluorescent chemical accumulates not only in the affected area, but also slightly in normal areas, the portion (background) other than the affected area emits weak fluorescence.

In this embodiment, the scope 2 is first inserted into the body cavity such that the distal end 2a thereof faces the examination target site X. When the light source 10 is activated in this state, white light containing excitation light emitted from the xenon lamp 11 and extracted by the excitation-light filter 13 is condensed by the coupling lens 15 and is guided to the distal end 2a of the scope 2 by the light-guide fiber 21. The white light is spread out onto the examination target site X by the spreading lens 23.

The fluorescent substance contained in the examination target site X is excited by the excitation light, emitting fluorescence, whereas the white light and part of the excitation light are reflected by the surface thereof. The fluorescence, the white light, and the excitation light are collected by the objective lens 31, and the beam splitter 33 reflects light with wavelengths longer than or equal to the examination wavelength, i.e., the excitation light and the fluorescence, and transmits white light with wavelengths shorter than the excitation wavelength.

Of the excitation light and the fluorescence reflected by the beam splitter 33, the excitation light is removed by the excitation-light cut filter 35, and only the fluorescence is focused by the focusing lens 37A and is captured by the fluorescence-image capturing section 38. In this manner, the fluorescence-image capturing section 38 acquires fluorescence image information from the examination target site X. The white light transmitted by the beam splitter 33 is focused by the focusing lens 37B and is captured by the white-light-image capturing section 39. In this manner, the white-light-image capturing section 39 acquires white-light image information from the examination target site X. Either the fluorescence image information or the white-light image information may be acquired first, or they may be acquired at the same time.

The white-light image information acquired by the white-light-image capturing section 39 is input to the reference-image generating section 41 of the image processor 40. The reference-image generating section 41 generates a two-dimensional white-light image based on the white-light image information.

The fluorescence image information acquired by the fluorescence-image capturing section 38 is input to the fluorescence-image generating section 42 of the image processor 40. The fluorescence-image generating section 42 generates a two-dimensional fluorescence image based on the fluorescence image information.

The fluorescence image and the white-light image generated by the fluorescence-image generating section 42 and the reference-image generating section 41 are input to the image-normalizing section 44 and are normalized using Eq. 1. The thus-normalized reference-light image and fluorescence image are converted into a correction reference-light image and a correction fluorescence image by the preprocessing section 46.

In this embodiment, the correction reference-light image is the normalized reference-light image multiplied by coefficient, and the correction fluorescence image is the normalized fluorescence image itself.

The divided-image generating section 43 divides the correction fluorescence image by the correction reference-light image to acquire a divided image.

The coefficient by which the normalized reference-light image is multiplied in the preprocessing section 46 is the ratio of a normalized fluorescence image to a normalized reference-light image acquired from a standard sample and is selected so that the distance characteristics of the fluorescence intensity of the normalized fluorescence image of the standard sample are equal to the distance characteristics of the return-light intensity of the normalized reference-light image of the same standard sample. Thus, by dividing the correction fluorescence image by the correction reference-light image obtained by multiplying the normalized reference-light image of the examination target site X by the coefficient, the divided-image generating section 43 can generate a divided image with sufficiently reduced dependence on examination distance.

Figure 4:
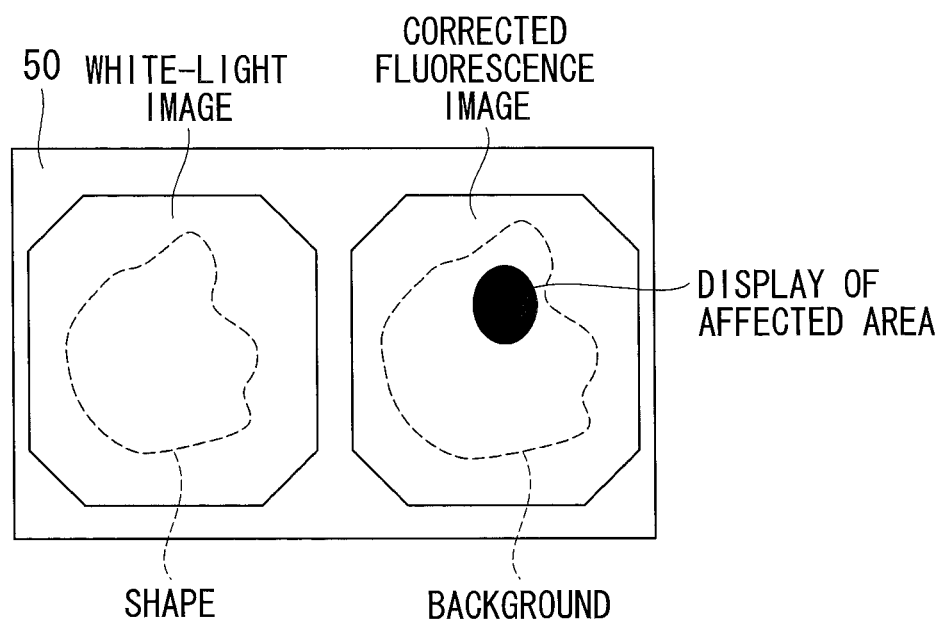
FIG. 4 is an illustration showing an example of a white-light image and a divided image displayed on a monitor in FIG. 1.

The thus-generated divided image (corrected fluorescence image) is fed to the threshold-setting section 45 and is also fed to and displayed on the monitor 50 together with the white-light image, as shown in FIG. 4.

Figure 5:
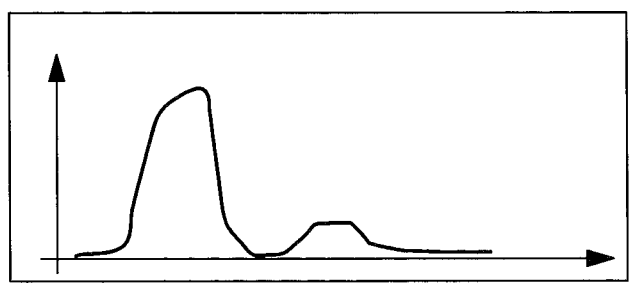
FIG. 5 is a histogram showing the relationship between the grayscale levels of the pixels in the divided image in FIG. 4 and the frequencies thereof in the entire image.

As shown in FIG. 5, the divided image is mainly composed of a region in which weak fluorescence from the background is displayed and a region in which strong fluorescence from the affected area is displayed. In this figure, the horizontal axis indicates the grayscale level, and the vertical axis indicates the frequency in the entire divided image. The monitor 50 may display a histogram as shown in FIG. 5.

In some cases, the influence of the examination distance on the divided image cannot be completely corrected for because fluorescence and reflected light differ in terms of their dependence on examination distance, which causes a certain error.

Figure 6:
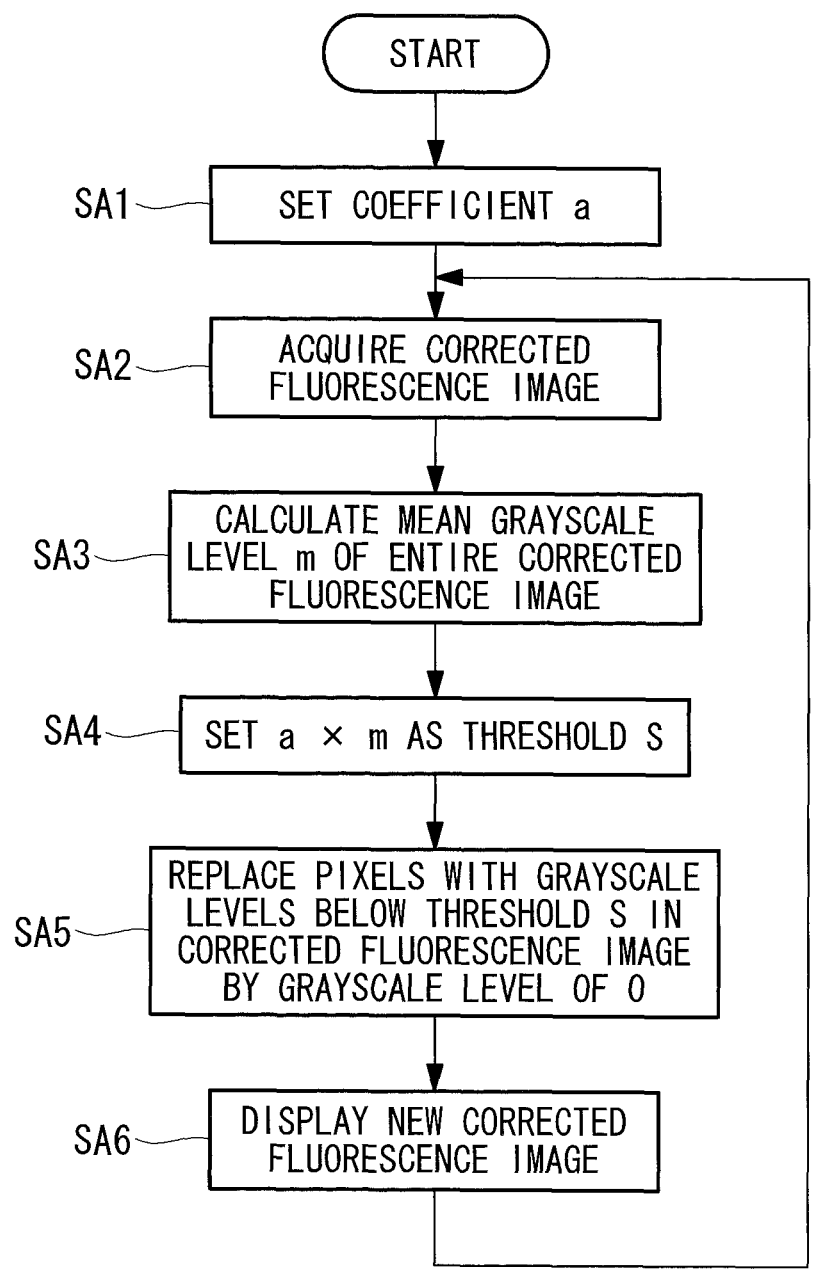
FIG. 6 is a flowchart showing the operation of the fluoroscopy apparatus in FIG. 1.

The setting of a threshold by the threshold-setting section 45 and the adjustment of a divided image by the image-adjusting section 51 for acquiring quantitative information about the examination target site X will be described below with reference to the flowchart shown in FIG. 6.

The threshold-setting section 45 determines, in advance, the coefficient a (for example, a=1.5) of calculation formula (1) above (step SA1). Upon receiving a divided image from the divided-image generating section 43 (step SA2), the threshold-setting section 45 calculates the mean grayscale level m of the entire image (step SA3).

The mean grayscale level m of the entire image is calculated, for example, using calculation formula (2) below.

{Eq. 3}

$$m = \frac{n_1 \times \overline{m_1} + n_2 \times \overline{m_2}}{n_1 + n_2} \quad (2)$$

$\overline{m_1}$ mean grayscale level of pixels displaying background
$\overline{m_2}$: mean grayscale level of pixels displaying affected area
$n_1$: total number of pixels displaying background
$n_2$: total number of pixels displaying affected area It is assumed that, if the total number of pixels of the divided image is 1,000,000 pixels, 950,000 pixels of those pixels display fluorescence from the background (total number of pixels of background $n_1$=950,000), and 50,000 pixels of those pixels display fluorescence from the affected area (total number of pixels of affected area $n_2$=50,000). It is assumed that, if the contrast of the fluorescent chemical is 1:2, the mean grayscale level $m_1$ of the background is 1,000, and the mean grayscale level $m_2$ of the affected area is 2,000.

With these assumptions, the threshold-setting section 45 calculates the mean grayscale level m of the entire image, i.e., 1,050, using calculation formula (2).

Based on the set coefficient a and the calculated mean grayscale level m of the entire image, the threshold-setting section 45 calculates the threshold S, i.e., 1,575, using calculation formula (1). In this manner, the threshold-setting section 45 sets the threshold S for the grayscale levels in the divided image (step SA4) and feeds the threshold S to the image-adjusting section 51.

Of all pixels in the divided image displayed on the monitor 50, the image-adjusting section 51 replaces pixels with grayscale levels below the threshold S, i.e., 1,575, by a grayscale level of 0 (step SA5). In this case, assuming that the distribution of the grayscale levels of the pixels displaying the background and the distribution of the grayscale levels of the pixels displaying the affected area are normal distributions and that the standard deviations thereof are ten times the square roots of the mean grayscale level of the pixels displaying the background and the mean grayscale level of the pixels displaying the affected area, 96.5% of the display of the background is deleted, and 82.9% of the display of the affected area remains.

Figure 7:
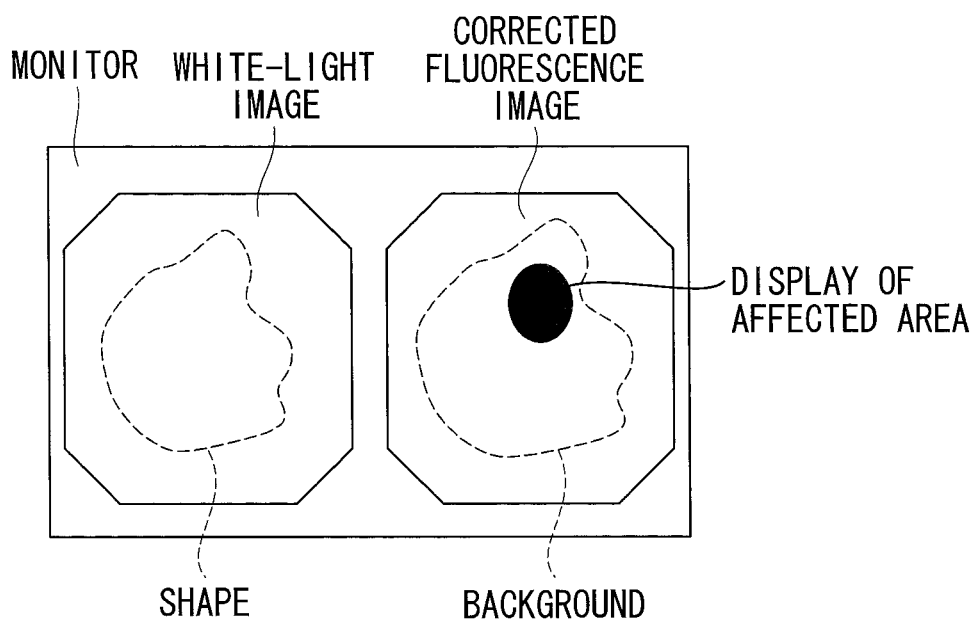
FIG. 7 is an illustration showing an example of a white-light image and a new divided image displayed on the monitor.
Figure 8:
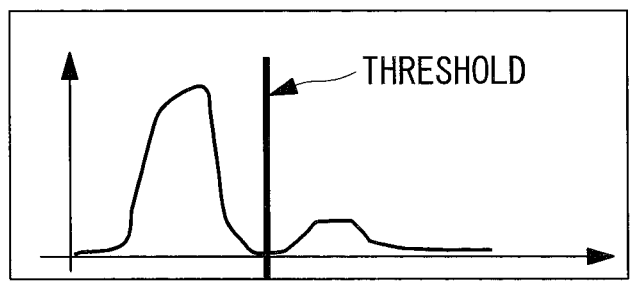
FIG. 8 is a histogram showing the relationship between the grayscale levels of the pixels in the divided image in FIG. 7 and the frequencies thereof in the entire image.

Thus, as shown in FIG. 7, a new divided image (corrected fluorescence image) with enhanced contrast between the region displaying the affected area and the region displaying the background is displayed on the monitor 50 (step SA6). As shown in FIG. 8, the new divided image is composed of a region in which fluorescence from mainly the affected area is displayed, which has higher grayscale levels than the threshold S.

Figure 9:
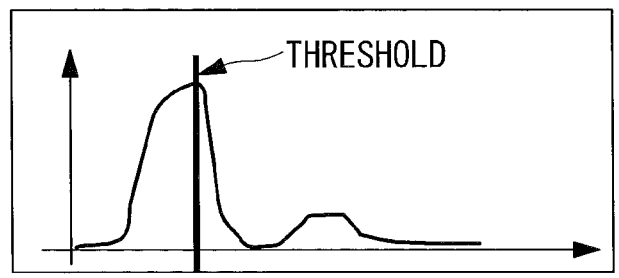
FIG. 9 is a histogram showing the relationship between the grayscale levels of the pixels in the divided image and the frequencies thereof in the entire image after the grayscale levels are varied.

Next, as shown in FIG. 9, the examination distance is varied, and accordingly the mean grayscale level of the pixels in a divided image of the next frame is varied to a higher level by an error factor. It is assumed that the mean grayscale level of the pixels displaying the background and the mean grayscale level of the pixels displaying the affected area are increased by 50%, i.e., $m_1=1,500$ and $m_2=3,000$, respectively.

Figure 10:
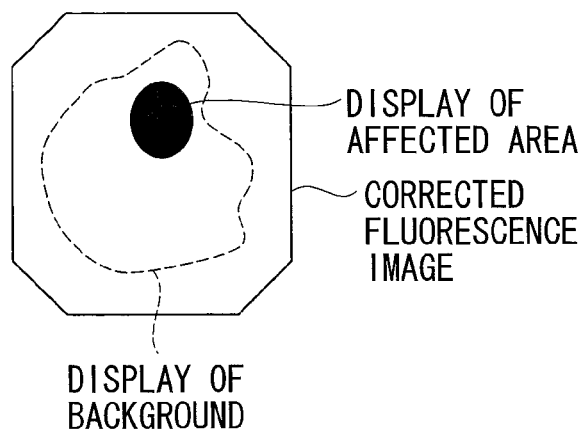
FIG. 10 is an illustration showing an example of the divided image in FIG. 9.

In this case, if the current threshold S remains at 1,575 without being changed after the variation in grayscale level, as shown in FIG. 10, 99.5% of the display of the affected area would remain, although only 57.7% of the display of the background would be deleted because of the larger region with grayscale levels above the threshold S, which would result in decreased sharpness of the divided image.

In this embodiment, steps SA2 to SA6 are repeated to set the threshold S based on the mean grayscale level m of the entire image in the threshold-setting section 45.

Figure 11:
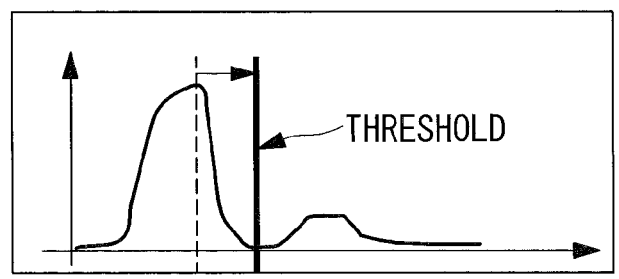
FIG. 11 is a histogram showing the relationship between the grayscale levels of the pixels in the divided image and the frequencies thereof in the entire image after image adjustment.

Upon receiving a divided image of the next frame (step SA2), the threshold-setting section 45 calculates the mean grayscale level m of the entire image of the next frame based on calculation formula (2) (step SA3) and, as shown in FIG. 11, sets a new threshold S, i.e., 2,363, which is higher than the threshold S of the preceding frame, i.e., 1,575 (step SA4).

Figure 12:
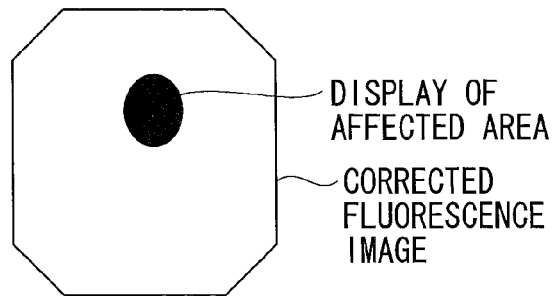
FIG. 12 is an illustration showing an example of the divided image in FIG. 11.

Thus, the grayscale levels in the divided image are adjusted by the image-adjusting section 51 (step SA5), and as shown in FIG. 12, a new divided image is displayed in which 98.7% of the display of the background is deleted, and 87.8% of the display of the affected area remains (step SA6).

In this manner, steps SA2 to SA6 are repeated, and when a divided image of the next frame is generated, the threshold S is updated based on the mean grayscale level m of the entire image, and a new divided image with adjusted grayscale levels is displayed on the monitor 50.

As described above, with the fluoroscopy apparatus 100 according to this embodiment, when the examination target site X is irradiated with the excitation light emitted from the light source 10, a fluorescence image of fluorescence emitted from the examination target site X is acquired by the fluorescence-image generating section 42, and when the examination target site X is irradiated with the reference light emitted together with the excitation light from the light source 10, a reference-light image of light returning therefrom is acquired by the reference-image generating section 41. The fluorescence image thus acquired is corrected by the divided-image generating section 43 using the reference-light image.

In this case, prior to correction by the divided-image generating section 43, the preprocessing section 46 multiplies at least one of the fluorescence image and the reference-light image by a coefficient by which the distance characteristics of fluorescence intensity and the distance characteristics of return-light intensity acquired from a standard sample in advance are made directly proportional to each other to generate a correction fluorescence image and a correction reference-light image.

Specifically, the fluorescence intensity of each pixel that forms the fluorescence image and the return-light intensity of each pixel that forms the reference-light image vary depending on the distance from the illuminating section to the positions corresponding to those pixels on the examination target site X and can be approximated by an exponential function of the distance. The distance dependence cannot be removed by directly dividing the fluorescence image by the reference-light image because the exponent of the distance characteristics of fluorescence intensity differs from the exponent of the distance characteristics of return-light intensity. Therefore, by raising the fluorescence intensity and the return-light intensity to the reciprocal of the exponent of the distance characteristics in advance, the distance characteristics of fluorescence intensity and the distance characteristics of return-light intensity can be made directly proportional to each other, thus allowing the distance dependence to be removed by division.

Accordingly, a coefficient by which at least one of the fluorescence image and the reference-light image is multiplied to provide the same effect as raising the fluorescence intensity and the return-light intensity to the reciprocal of the exponent, as described above, is determined in advance from the distance characteristics of fluorescence intensity and the distance characteristics of return-light intensity acquired from a standard sample in advance. At least one of the fluorescence image and the reference-light image is then multiplied by the resulting coefficient to generate a correction fluorescence image and a correction reference-light image. By dividing the correction fluorescence image by the correction reference-light image, the divided-image generating section 43 can generate a divided image corrected to result in sufficiently reduced distance dependence.

The image-adjusting section 51 then adjusts the grayscale levels of the divided image based on the predetermined threshold for enhanced contrast between the affected area and the background, thus acquiring a sharp divided image with a reduced influence of weak fluorescence emitted from the background.

Because this embodiment uses a white-light image generated from light reflected from the subject and light scattered back from the subject as the reference-light image, the grayscale levels of the reference-light image are not zero or near zero even in a region where almost no fluorescence occurs, thus allowing an accurate divided image to be generated.

Because the threshold-setting section 45 sets a threshold based on the mean grayscale level of the divided image, the threshold can be updated with variations in grayscale level in the divided image, thereby maintaining the sharpness of each acquired divided image. Thus, quantitative information about the examination target site X can be acquired.

Although the coefficient a=1.5 is illustrated and described in this embodiment, the coefficient a may be changed depending on the examination conditions.

Although this embodiment employs a coefficient by which the distance characteristics of return-light intensity for a standard sample are made equal to the distance characteristics of fluorescence intensity, the coefficient is not limited thereto, but may be a coefficient by which both characteristics are made directly proportional.

Although this embodiment employs a configuration for highly quantitative fluorescence examination with reduced dependence on examination distance, it may be replaced by a configuration for reduced dependence on examination angle. Specifically, the preprocessing section 46 multiplies the normalized reference-light image of the examination target site X by a coefficient that is the ratio of a normalized fluorescence image to a normalized reference-light image acquired from a standard sample with varying examination angles and that is selected so that the angle characteristics of the fluorescence intensity of the normalized fluorescence image of the standard sample are directly proportional to the angle characteristics of the return-light intensity of the normalized reference-light image of the same standard sample. By dividing the correction fluorescence image by the resulting correction reference-light image, the divided-image generating section 43 can generate a divided image corrected to result in sufficiently reduced dependence on examination angle, thus allowing highly quantitative fluorescence examination.

First Modification

This embodiment can be modified as follows.

For example, although in this embodiment the threshold-setting section 45 sets a threshold based on the mean grayscale level m of the entire divided image, as a first modification, the threshold-setting section 45 may set the threshold S based on the sum of the mean grayscale level m and the standard deviation of the entire image, as shown in calculation formula (3) below.

{Eq. 4}

$$S = m + \sigma \quad (3)$$

σ: standard deviation of grayscale levels of individual pixels in divided image

The standard deviation σ of the entire image may be calculated using calculation formula (4) below.

{Eq. 5}

$$\sigma^2 = \overline{x^2} - m^2 \quad (4)$$
$$= \frac{n_1 \times \overline{x_1^2} + n_2 \times \overline{x_2^2}}{n_1 + n_2} - m^2$$
$$= \frac{n_1(\sigma_1^2 + m_1^2) + n_2(\sigma_2^2 + m_2^2)}{n_1 + n_2} - m^2$$

$\overline{x^2}$: mean square of grayscale levels of entire image
$\overline{x_1^2}$: mean square of grayscale levels of background
$\overline{x_2^2}$: mean square of grayscale levels of affected area
$\sigma_1$: standard deviation of grayscale levels of pixels displaying background
$\sigma_2$: standard deviation of grayscale levels of pixels displaying affected area The standard deviation $\sigma_1$ of the background and the standard deviation $\sigma_2$ of the affected area are each ideally close to the square root of the mean grayscale level, although they fluctuate largely, for example, due to fluctuations in the luminous intensity distribution of the illumination and surface irregularities in the examination target site X. Accordingly, assuming that the standard deviations $\sigma_1$ and $\sigma_2$ are ten times the ideal value (the square root of the mean grayscale level), the standard deviation $\sigma_1$ of the background is 316, and the standard deviation $\sigma_2$ of the affected area is 447.

Figure 13:
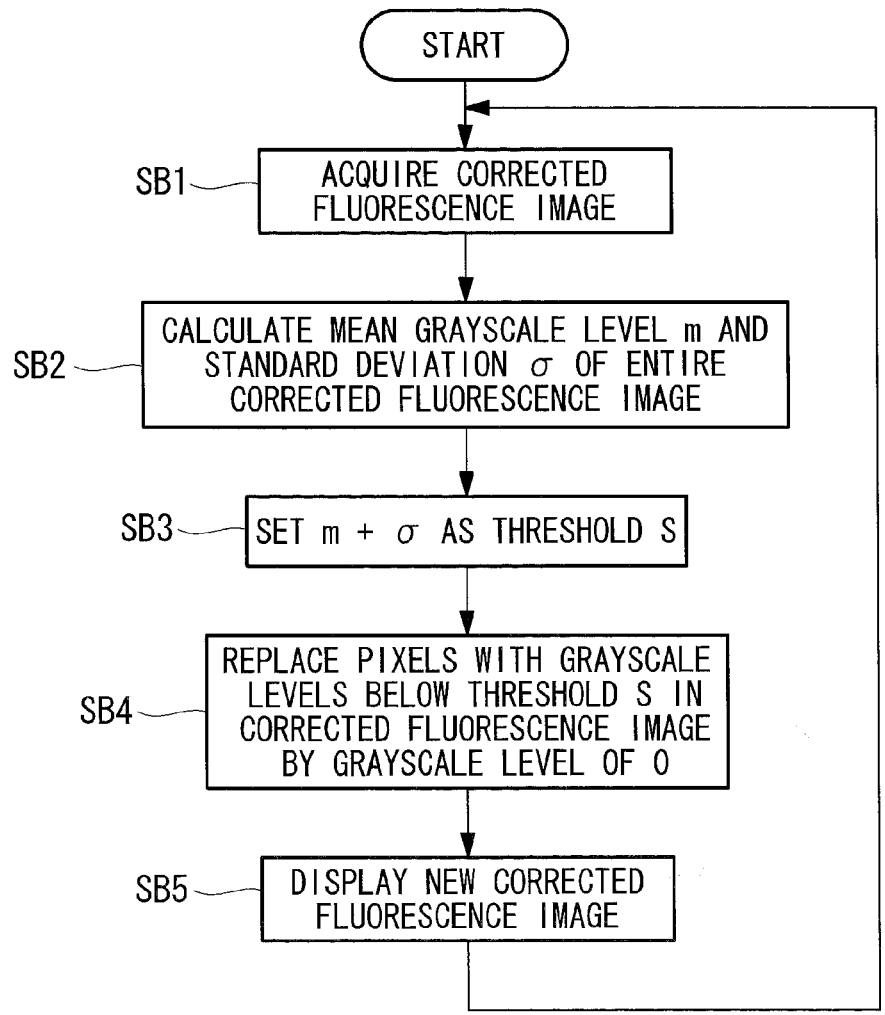
FIG. 13 is a flowchart showing the operation of a fluoroscopy apparatus according to a first modification.

With this assumption, as shown in the flowchart in FIG. 13, upon receiving a divided image (step SB1), the threshold-setting section 45 calculates the mean grayscale level m of the entire image, i.e., 1,050, and the standard deviation o, i.e., 391, using calculation formulae (2) and (4) (step SB2). Based on the calculated mean grayscale level m and standard deviation σ of the entire image, the threshold-setting section 45 calculates the threshold S, i.e., 1,441, using calculation formula (3) and sets the threshold S (step SB3).

Of all pixels in the divided image, the image-adjusting section 51 replaces pixels with grayscale levels below the threshold S, i.e., 1,441, by a grayscale level of 0 (step SB4). Thus, a new divided image in which 91.8% of the display of the background is deleted and 89.5% of the display of the affected area remains is displayed on the monitor 50 (step SB5).

Next, when the examination distance is varied, and accordingly the mean grayscale level of the pixels in a divided image of the next frame is varied to a higher level by an error factor, if the threshold S remains at 1,441 without being changed, 98.8% of the display of the affected area would remain after the variation in grayscale level, although only 65.2% of the display of the background would be deleted, which would result in decreased sharpness of the divided image.

In this modification, steps SB1 to SB5 are repeated to set the threshold S based on the sum of the mean grayscale level m and the standard deviation σ of the entire image in the threshold-setting section 45.

For example, if the mean grayscale level of the pixels is varied by 30%, it can be assumed that the mean grayscale level $m_1$ of the background is 1,300, the standard deviation $\sigma_1$ is 361, the mean grayscale level $m_2$ of the affected area is 2,600, and the standard deviation $\sigma_2$ is 510.

Upon receiving a divided image of the next frame (step SB1), the threshold-setting section 45 calculates the mean grayscale level m of the entire image of the next frame, i.e., 1,365, and the standard deviation σ, i.e., 466, based on calculation formulae (2) and (4) (step SB2) and sets a new threshold S, i.e., 1,831, based on calculation formula (3) (step SB3). Thus, the grayscale levels in the divided image are adjusted by the image-adjusting section 51 (step SB4), and a new divided image is displayed in which 92.9% of the display of the background is deleted, and 93.4% of the display of the affected area remains (step SB5).

As described above, because the fluoroscopy apparatus according to this modification sets the threshold S based on the sum of the mean grayscale level m and the standard deviation σ of the entire image, a sharp divided image can always be acquired even if an examination distance error factor remains in the divided image. In addition, even if the grayscale levels of the pixels in the divided image vary, a more precise threshold can be set than in the case where a threshold is set based only on the mean grayscale level.

A comparative example of this modification will be described below.

For example, it is assumed that the mean grayscale level of the pixels is varied by 30%, and accordingly the mean grayscale level $m_1$ of the background is 700, the standard deviation $\sigma_f$ is 265, the mean grayscale level $m_2$ of the affected area is 1,400, and the standard deviation $\sigma_2$ is 374. In this case, as a comparative example, if the threshold S is calculated based only on the mean grayscale level m of the entire image, the threshold S is 1,103, and 93% of the display of the background is deleted, although only 78% of the display of the affected area remains.

In contrast, as in this modification, if the threshold S is calculated based on the sum of the mean grayscale level m and the standard deviation σ of the entire image, the threshold S is 1,046, and 90% of the display of the background is deleted, with 83% of the display of the affected area remaining. Thus, it is possible to set a threshold that allows more of the display of the affected area to remain, which is particularly effective if sensitivity has priority over specificity.

Alternatively, the threshold may be set by multiplying the mean m and the standard deviation σ by any coefficients a and b, respectively, as shown in the following equation:

$$S=am+b\sigma$$

This allows a more optimal threshold S to be calculated depending on the purpose of examination; for example, smaller coefficients a and b may be used if not missing an affected area (high sensitivity) has priority, and larger coefficients a and b may be used if not displaying a portion other than an affected area (high specificity) has priority.

Second Modification

Figure 14:
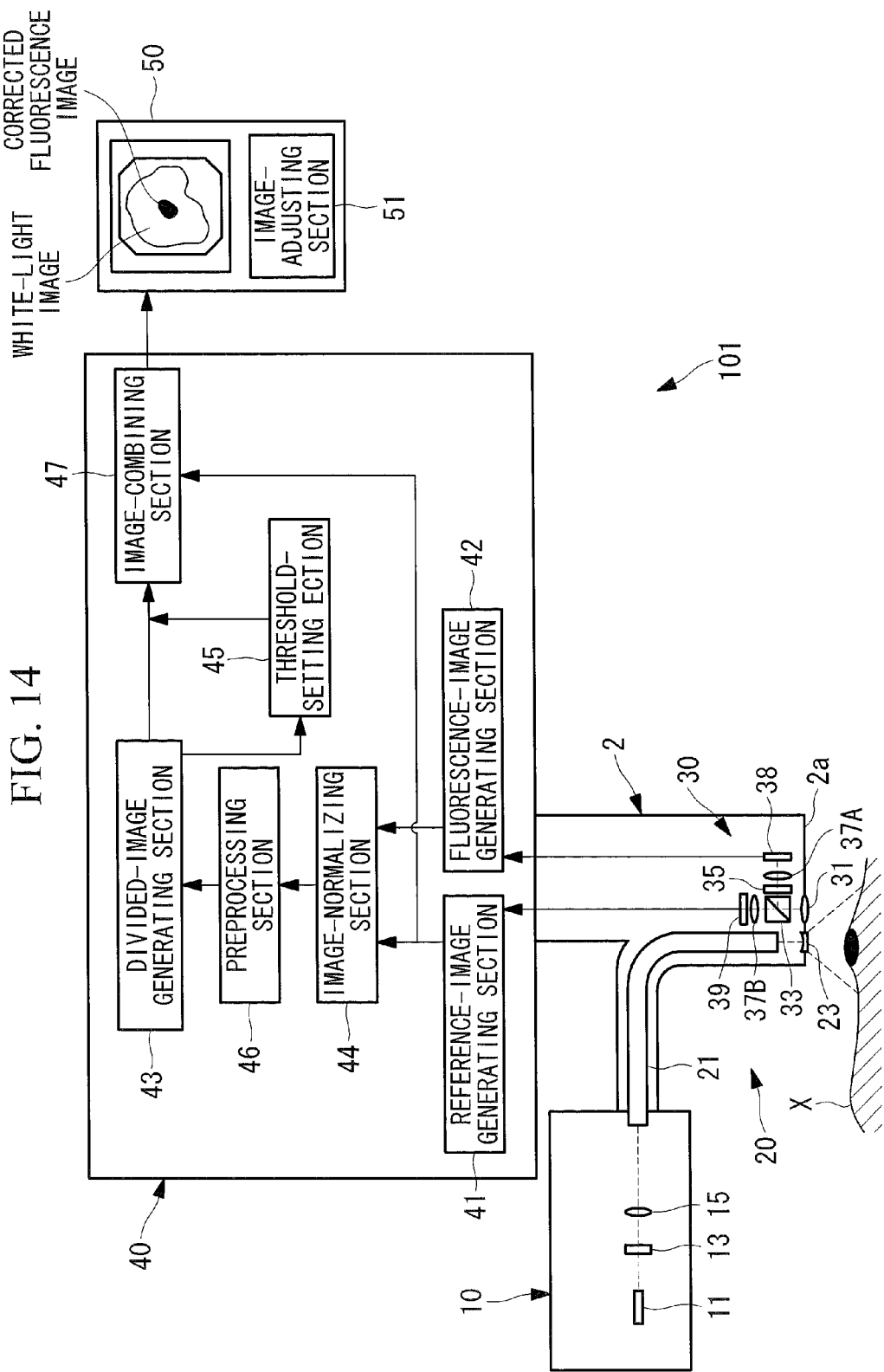
FIG. 14 is a schematic block diagram of a fluoroscopy apparatus according to a second modification.

As a second modification of this embodiment, as shown in FIG. 14, an image-combining section 47 that generates a combined image of a white-light image and a divided image may be provided, and the resulting combined image may be displayed on the monitor 50.

Figure 15:
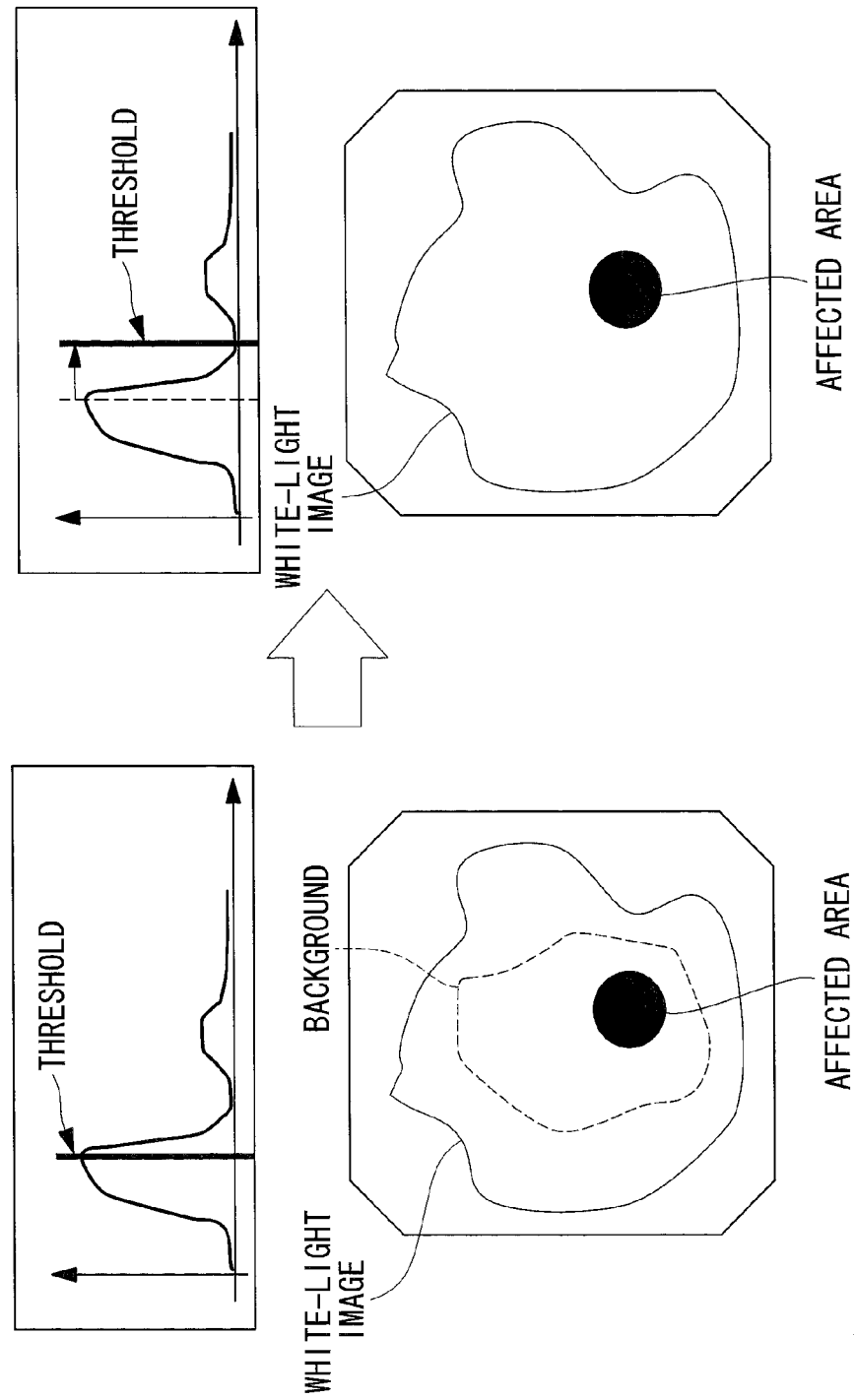
FIG. 15 is an illustration illustrating an advantage of the fluoroscopy apparatus in FIG. 14.

A fluoroscopy apparatus 101, having the above configuration, according to this modification can more clearly present the positional relationship between the white-light image and the divided image to the operator. Because the region below the threshold is displayed as having a grayscale level of 0, the divided image does not interfere with the display of the white-light image in the region other than the affected area in the combined image in which both images are superimposed, as shown in FIG. 15.

Third Modification

A third modification of this embodiment will be described below.

Figure 16:
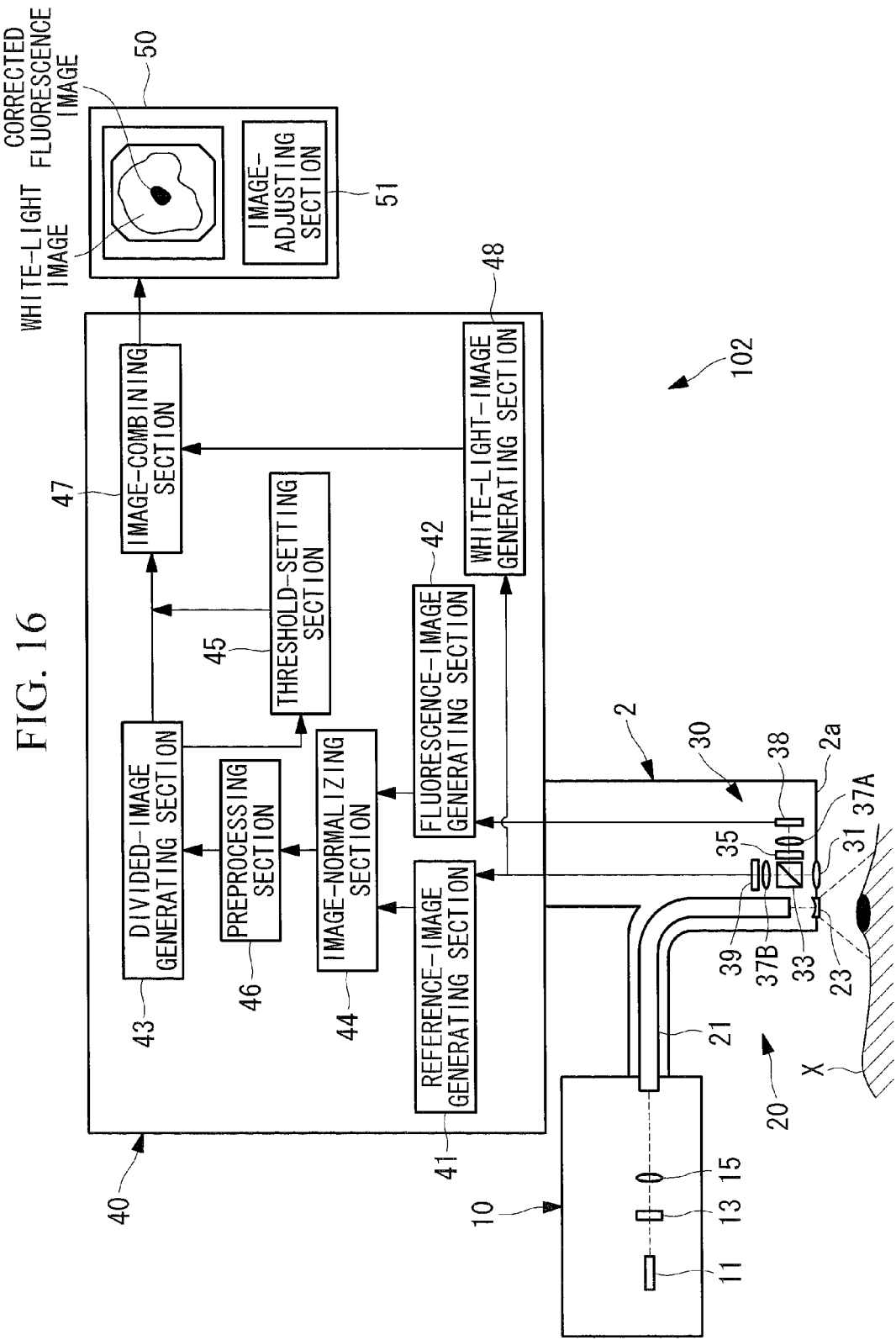
FIG. 16 is a schematic block diagram of a fluoroscopy apparatus according to a third modification.

Whereas the embodiment described above uses a white-light image as a reference-light image, as shown in FIG. 16, a fluoroscopy apparatus 102 according to this modification combines a divided image (corrected fluorescence image) with a white-light image generated, for example, by a CCD or CMOS sensor (white-light-image acquiring section) composed of three RGB channels and a white-light-image generating section 48.

In this case, a method such as using only the R channel as a reference-light image may be used.

Alternatively, it is possible to use a method in which the examination target site X is separately irradiated with light in a wavelength range different from that of white light, such as infrared or near-infrared light, as reference light, to acquire a reference-light image separately from the white-light image. In any case, the white-light image and the divided image are simultaneously displayed; therefore, information about the divided image can be further presented to the operator without interfering with examination based on the white-light image.

Fourth Modification

A fourth modification of this embodiment will be described below.

Figure 17:
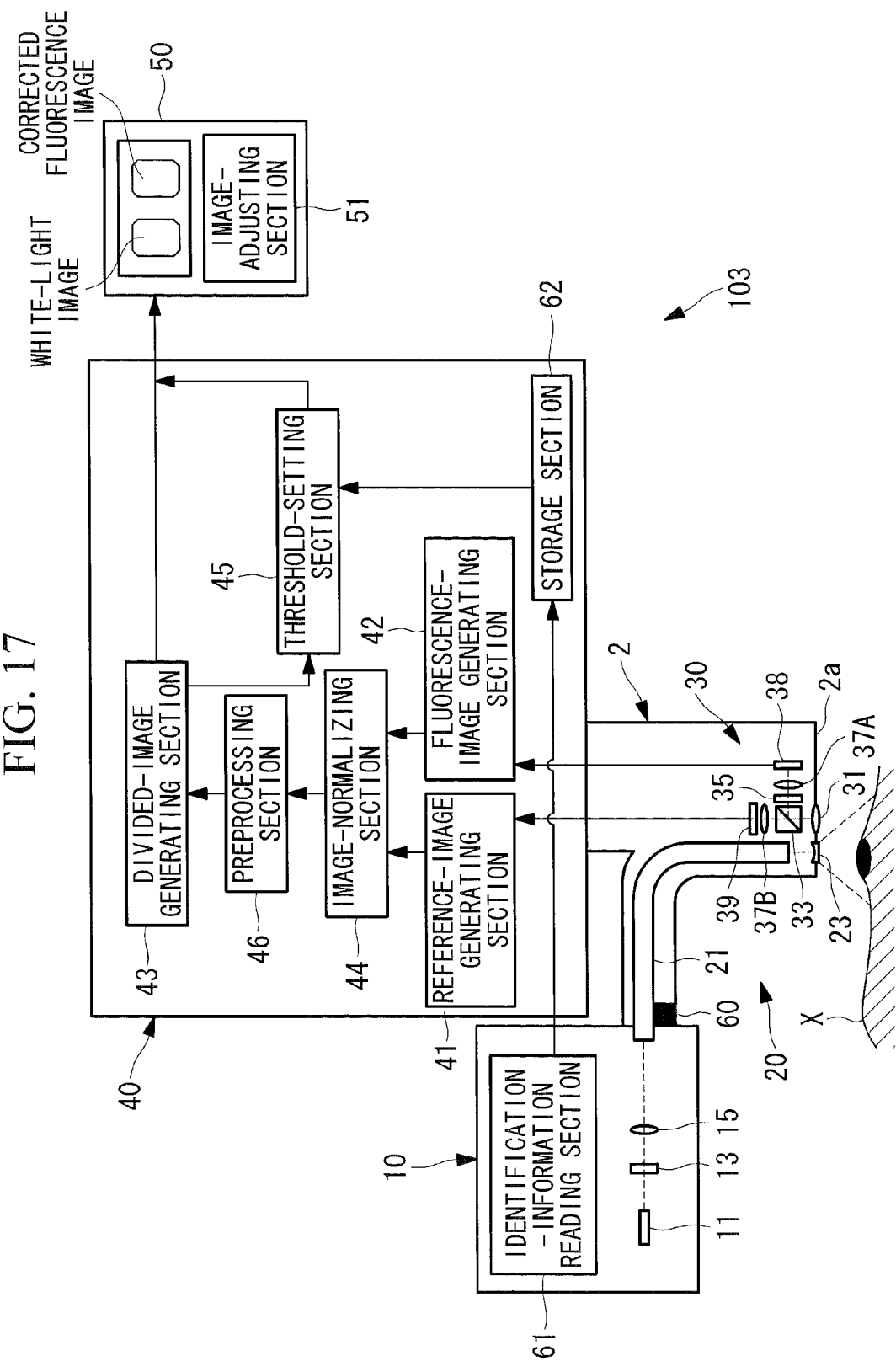
FIG. 17 is a schematic block diagram of a fluoroscopy apparatus according to a fourth modification.

As the fourth modification of this embodiment, as shown in FIG. 17, an insertion part (attachable and detachable component) 2 may be provided so as to be attachable to and detachable from the light source 10. In this case, the insertion part 2 is attached and detached and is replaced with another insertion part 2 to change the various optical systems, such as the objective lens 31, contained in the insertion part 2; thus, the coefficient changes, for example, with changes in the numerical aperture (NA) and pupil diameter of the objective lens 31 and with changes in the wavelength of the fluorescence detected and the examination target site (such as tissue of the stomach or the large intestine).

Accordingly, a fluoroscopy apparatus 103 according to this modification has an IC chip 60 that stores identification information in the insertion part 2 and an identification-information reading section 61 that reads the identification information from the IC chip 60 in the light source 10 to which the insertion part 2 is attached. The image processor 40 includes a storage section 62 that stores the identification information from the IC chip 60 in association with a coefficient suitable for the insertion part 2.

The preprocessing section 46 may receive the coefficient corresponding to the identification information for the insertion part 2 from the storage section 62 and execute the operation described above.

This allows an optimum coefficient for the insertion part 2 to be set when the insertion part 2 is replaced relative to the light source 10 so that a highly quantitative divided image can always be acquired.

The storage section 62 may store a coefficient by which a normalized fluorescence image is multiplied, rather than a coefficient by which a normalized reference-light image is multiplied, or may store a coefficient by which a normalized reference-light image is multiplied and a coefficient by which a normalized fluorescence image is multiplied.

Alternatively, the threshold may be set as follows:

$$S=am+b\sigma$$

and the storage section 62 may store the coefficients a and b for setting the threshold in addition to the coefficients for distance and angle dependence correction.

Although this modification employs a configuration for highly quantitative fluorescence examination with reduced dependence on examination distance, the configuration may be replaced by a configuration for reduced dependence on examination angle.

Second Embodiment

Next, a fluoroscopy system 70 according to a second embodiment of the present invention will be described below with reference to the drawings.

In the description of this embodiment, the portions having the same structure as those of the fluoroscopy apparatus 100 according to the first embodiment described above are labeled with the same reference signs, and a description thereof is omitted.

Figure 18:
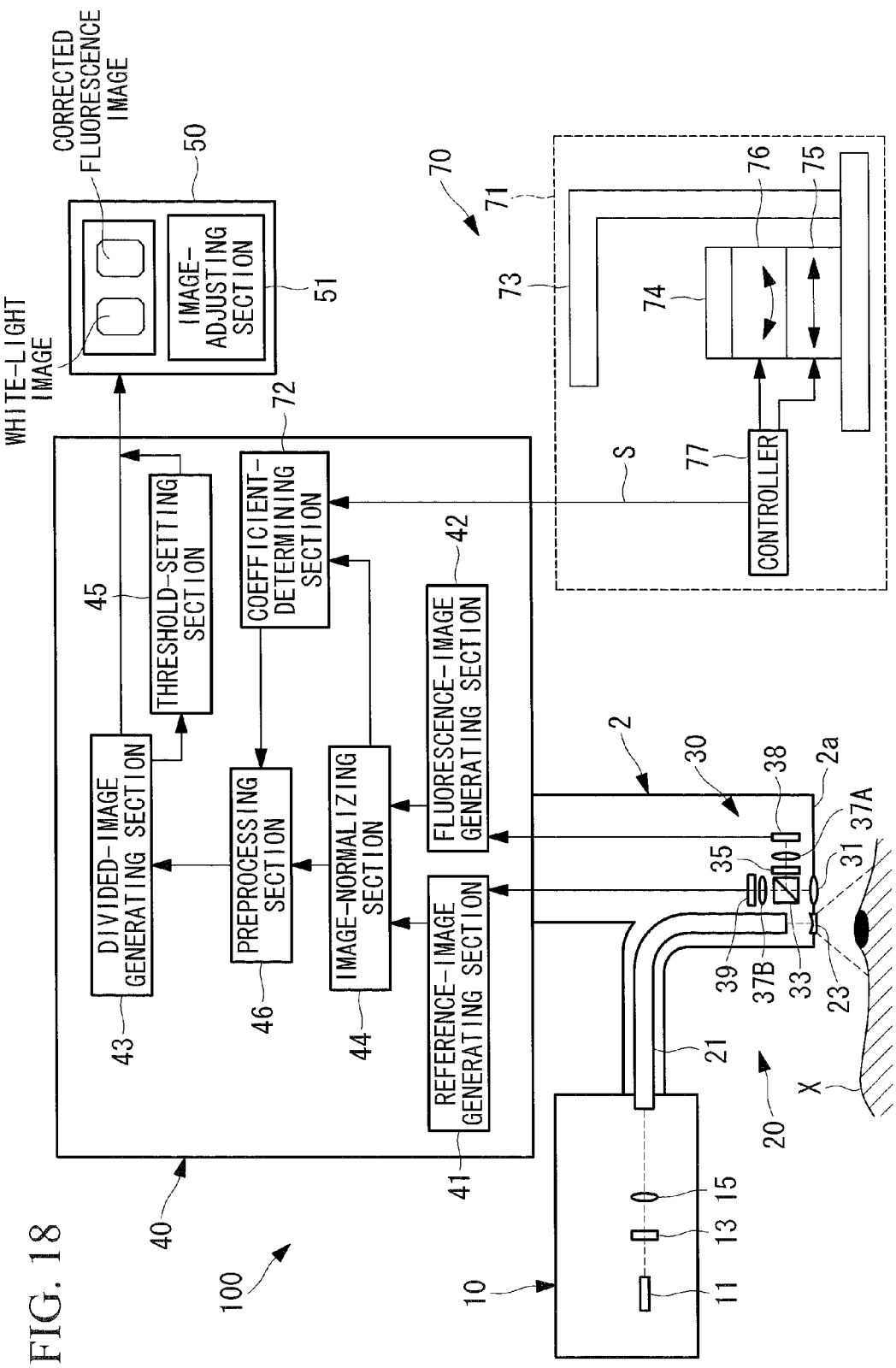
FIG. 18 is a schematic block diagram of a fluoroscopy system according to a second embodiment of the present invention.

As shown in FIG. 18, the fluoroscopy system 70 according to this embodiment includes a fluoroscopy apparatus 100 and a calibration device 71 to which the fluoroscopy apparatus 100 is mounted.

In this embodiment, the fluoroscopy apparatus 100 includes a coefficient-determining section 72 that calculates a coefficient.

Figure 19:
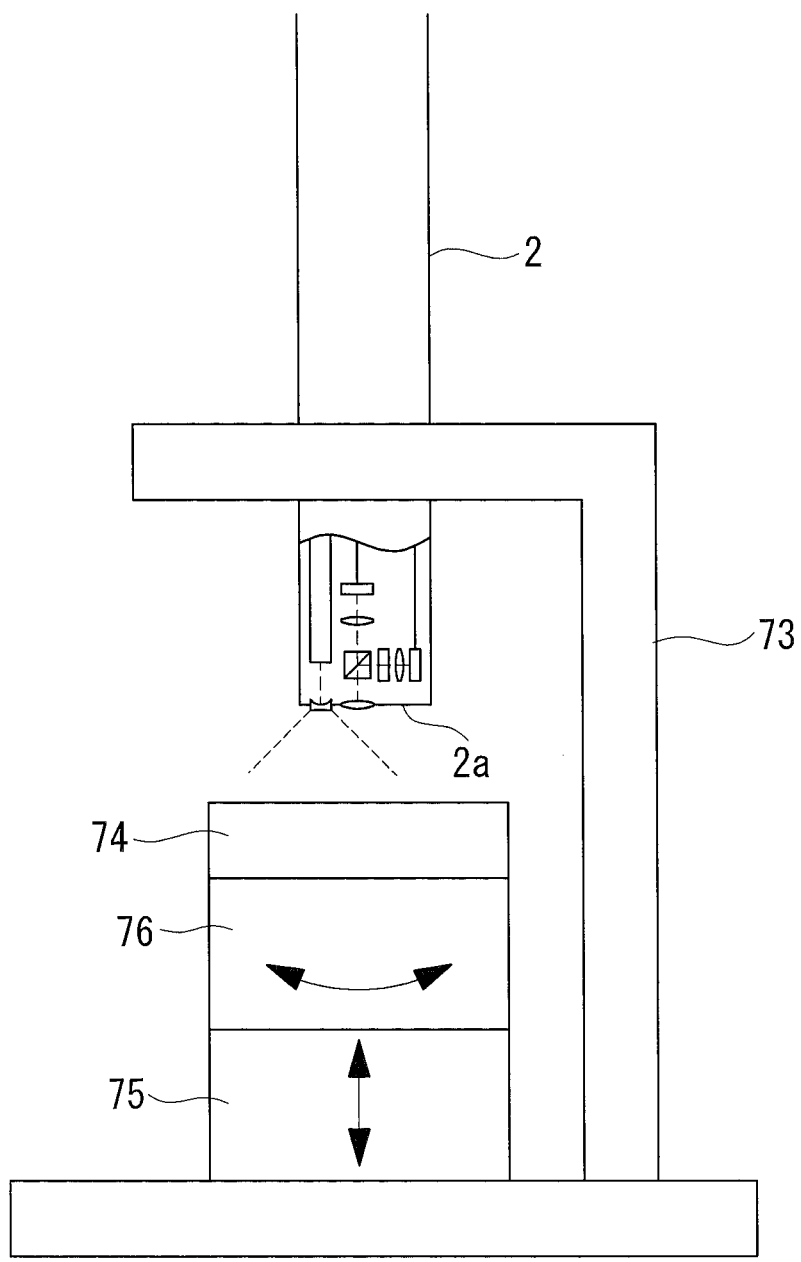
FIG. 19 is an illustration showing a calibration device of the fluoroscopy system in FIG. 18.

As shown in FIGS. 18 and 19, the calibration device 71 includes a holder 73 that holds the insertion part 2, standard sample 74 placed at an examination distance opposite the distal end surface 2a of the insertion part 2 held by the holder 73, a linear-motion stage 75 that changes the examination distance between the distal end surface 2a of the insertion part 2 and the standard sample 74, a tilt stage 76 that changes the angle (examination angle) of the surface of the standard sample 74 to the optical axis of the objective lens 31, and a controller 77 that controls these stages 75 and 76.

The controller 77 actuates the stages 75 and 76 to change the examination distance or the examination angle and outputs a trigger signal S at a preset timing.

The coefficient-determining section 72 receives a normalized fluorescence image and a normalized reference-light image from the image-normalizing section 44, stores the luminance of the normalized fluorescence image and the luminance of the normalized reference-light image at the time when the coefficient-determining section 72 receives the trigger signal S from the controller 77, calculates a coefficient by dividing the luminance of the normalized fluorescence image by the luminance of the normalized reference-light image, and stores the calculated coefficient in association with the luminance of the normalized reference-light image.

To acquire a coefficient after the examination distance is changed, as shown in FIG. 19, the controller 77 first actuates the linear-motion stage 75 so that the distal end surface 2a of the insertion part 2 is located at an examination start distance from the surface of the standard sample 74. The illumination unit 20 then irradiates the standard sample 74 with illumination light and excitation light so that return light and fluorescence are captured, and the controller 77 outputs a trigger signal S each time and moves the stage 75 by a predetermined distance. In this manner, the coefficient-determining section 72 stores a plurality of coefficients acquired at a plurality of different examination distances in association with the luminances of the normalized reference-light images.

To acquire a coefficient after the examination angle is changed, as shown in FIG. 19, the controller 77 first actuates the linear-motion stage 75 and the tilt stage 76 so that the distal end surface 2a of the insertion part 2 is located at an examination start distance and angle from the surface of the standard sample 74. The illumination unit 20 then irradiates the standard sample 74 with illumination light and excitation light so that return light and fluorescence are captured, and the controller 77 outputs a trigger signal S each time and moves the tilt stage 76 by a predetermined distance. In this manner, the coefficient-determining section 72 stores a plurality of coefficients acquired at a plurality of different examination angles in association with the luminances of the normalized reference-light images.

The coefficients acquired after the examination distance is changed and the coefficients acquired after the examination angle is changed may be selected depending on the examination conditions.

When the luminance of a normalized reference-light image is input from the image-normalizing section 44, the coefficient-determining section 72 calculates the coefficient corresponding to the luminance and outputs the coefficient to the preprocessing section 46. Specifically, the coefficient-determining section 72 stores a plurality of coefficients associated with the luminances of a plurality of normalized reference-light images at intervals, and if a luminance between the intervals is input, the coefficient-determining section 72 calculates a new coefficient by interpolating the coefficients corresponding to the luminances between which the input luminance falls and outputs the new coefficient to the preprocessing section 46.

In this manner, the fluoroscopy system 70 according to this embodiment can set a coefficient depending on changes in the examination target and the examination conditions, such as the individual optical systems and the fluorescence wavelength used for examination, each time they change, thus allowing examination with a highly quantitative fluorescence image for various examination targets under various examination conditions.

For example, if the fluoroscopy apparatus 100 is applied to an endoscope, the fluoroscopy system 70 can set an optimum coefficient depending on, for example, differences in the type of endoscope, such as a rigid endoscope or flexible endoscope, and the type of examination site, such as an upper gastrointestinal endoscope or lower gastrointestinal endoscope. For the same type of fluoroscopy apparatus 100, the fluoroscopy system 70 can set a coefficient for each individual apparatus irrespective of differences between individual apparatuses.

The standard sample 74 used in this embodiment may be a phantom that has scattering and absorption properties similar to those of the living body to be examined or may be tissue cut from a human or animal (such as a pig or mouse).

Although embodiments of the present invention have been described in detail above with reference to the drawings, the specific configurations thereof are not limited to these embodiments, but encompass design changes that do not depart from the scope of the present invention. For example, the present invention is not limited to the above embodiments and modifications, but encompasses various combinations of these embodiments and modifications without limitation.

Although the image-adjusting section 51 deletes the display of the fluorescence from the background and leaves the display of the affected area in the above embodiments and modifications, it may enhance the contrast between the fluorescence from the affected area and the fluorescence from the background, for example, by decreasing the grayscale levels of the pixels displaying the background so as not to delete the display of the background or by increasing the grayscale levels of the pixels displaying the affected area.

The following aspect of invention is derived from the embodiment and modifications thereof described above.

A first aspect of the present invention is a fluoroscopy apparatus including a light source that irradiates a subject with excitation light and reference light; a fluorescence-image acquiring section that captures fluorescence emitted from the subject irradiated with the excitation light from the light source to acquire a fluorescence image; a reference-light-image acquiring section that captures return light returning from the subject irradiated with the reference light from the light source to acquire a reference-light image; a preprocessing section that multiplies at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image; a divided-image generating section that divides the correction fluorescence image generated by the preprocessing section by the correction reference-light image to generate a divided image; a threshold-setting section that sets a threshold based on a mean grayscale level of pixels in the divided image generated by the divided-image generating section; an image-adjusting section that enhances contrast between a region with grayscale levels above the threshold set by the threshold-setting section and a region with grayscale levels below the threshold in the divided image; and a display that displays the divided image with the contrast enhanced by the image-adjusting section.

According to the first aspect of the present invention, when the subject is irradiated with the excitation light emitted from the light source, a fluorescence image of fluorescence emitted from the subject is acquired by the fluorescence-image acquiring section, and when the subject is irradiated with the reference light emitted together with the excitation light from the light source, a reference-light image of light returning therefrom is acquired by the reference-light-image acquiring section. The fluorescence image thus acquired is corrected by the divided-image generating section using the reference-light image.

In this case, prior to correction by the divided-image generating section, the preprocessing section multiplies at least one of the fluorescence image and the reference-light image by a coefficient by which the distance characteristics of fluorescence intensity and the distance characteristics of return-light intensity acquired from a standard sample in advance are made directly proportional to each other to generate a correction fluorescence image and a correction reference-light image.

Specifically, the fluorescence intensity of each pixel that forms the fluorescence image and the return-light intensity of each pixel that forms the reference-light image vary depending on the distance from the illuminating section to the positions corresponding to those pixels on the subject and can be approximated by an exponential function of the distance. The distance dependence cannot be removed by directly dividing the fluorescence image by the reference-light image because the exponent of the distance characteristics of fluorescence intensity differs from the exponent of the distance characteristics of return-light intensity. Therefore, by raising the fluorescence intensity and the return-light intensity to the reciprocal of the exponent of the distance characteristics in advance, the distance characteristics of fluorescence intensity and the distance characteristics of return-light intensity can be made directly proportional to each other, thus allowing the distance dependence to be removed by division.

Accordingly, a coefficient by which at least one of the fluorescence image and the reference-light image is multiplied to provide the same effect as raising the fluorescence intensity and the return-light intensity to the reciprocal of the exponent, as described above, is determined in advance from the distance characteristics of fluorescence intensity and the distance characteristics of return-light intensity acquired from a standard sample in advance. At least one of the fluorescence image and the reference-light image is then multiplied by the resulting coefficient to generate a correction fluorescence image and a correction reference-light image. By dividing the correction fluorescence image by the correction reference-light image, the divided-image generating section can generate a divided image corrected to result in sufficiently reduced distance dependence.

In some cases, the influence of the examination distance cannot be completely corrected for because reference light and excitation light differ in terms of their dependence on examination distance, which causes a certain error in the divided image. In such cases, a divided image in which the contrast between a region with grayscale levels above the threshold and a region with grayscale levels below the threshold is enhanced by the image-adjusting section can be displayed on the display, thus acquiring a sharp divided image with a reduced influence of weak fluorescence emitted from the background.

When the examination distance, for example, is varied, and accordingly the grayscale levels of the pixels in the divided image are varied by an error factor, the threshold-setting section can update the threshold with the variation in grayscale level, and the image-adjusting section can thereby maintain the sharpness of the divided image. Thus, quantitative information about the subject can be acquired.

That is, the first aspect allows highly quantitative fluorescence examination with precisely reduced distance dependence.

A second aspect of the present invention is a fluoroscopy apparatus including a light source that irradiates a subject with excitation light and reference light; a fluorescence-image acquiring section that captures fluorescence emitted from the subject irradiated with the excitation light from the light source to acquire a fluorescence image; a reference-light-image acquiring section that captures return light returning from the subject irradiated with the reference light from the light source to acquire a reference-light image; a preprocessing section that multiplies at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image; a divided-image generating section that divides the correction fluorescence image generated by the preprocessing section by the correction reference-light image to generate a divided image; a threshold-setting section that sets a threshold based on a mean grayscale level of pixels in the divided image generated by the divided-image generating section; an image-adjusting section that enhances contrast between a region with grayscale levels above the threshold set by the threshold-setting section and a region with grayscale levels below the threshold in the divided image; and a display that displays the divided image with the contrast enhanced by the image-adjusting section.

According to the second aspect of the present invention, when the subject is irradiated with the excitation light emitted from the light source, a fluorescence image of fluorescence emitted from the subject is acquired by the fluorescence-image acquiring section, and when the subject is irradiated with the reference light emitted together with the excitation light from the light source, a reference-light image of light returning therefrom is acquired by the reference-light-image acquiring section. The fluorescence image thus acquired is corrected by the divided-image generating section using the reference-light image.

In this case, prior to correction by the divided-image generating section, the preprocessing section multiplies at least one of the fluorescence image and the reference-light image by a coefficient by which the angle characteristics of fluorescence intensity and the angle characteristics of return-light intensity acquired from a standard sample in advance are made directly proportional to each other to generate a correction fluorescence image and a correction reference-light image.

Specifically, the fluorescence intensity of each pixel that forms the fluorescence image and the return-light intensity of each pixel that forms the reference-light image vary depending on the angle from the illuminating section to the positions corresponding to those pixels on the subject and can be approximated by an exponential function of the angle. The angle dependence cannot be removed by directly dividing the fluorescence image by the reference-light image because the exponent of the angle characteristics of fluorescence intensity differs from the exponent of the angle characteristics of return-light intensity. Therefore, by raising the fluorescence intensity and the return-light intensity to the reciprocal of the exponent of the angle characteristics in advance, the angle characteristics of fluorescence intensity and the angle characteristics of return-light intensity can be made directly proportional to each other, thus allowing the angle dependence to be removed by division.

Accordingly, a coefficient by which at least one of the fluorescence image and the reference-light image is multiplied to provide the same effect as raising the fluorescence intensity and the return-light intensity to the reciprocal of the exponent, as described above, is determined in advance from the angle characteristics of fluorescence intensity and the angle characteristics of return-light intensity acquired from a standard sample in advance. At least one of the fluorescence image and the reference-light image is then multiplied by the resulting coefficient to generate a correction fluorescence image and a correction reference-light image. By dividing the correction fluorescence image by the correction reference-light image, the divided-image generating section can generate a divided image corrected to result in sufficiently reduced angle dependence.

In some cases, the influence of the examination angle cannot be completely corrected for because reference light and excitation light differ in terms of their dependence on examination angle, which causes a certain error in the divided image. In such cases, a divided image in which the contrast between a region with grayscale levels above the threshold and a region with grayscale levels below the threshold is enhanced by the image-adjusting section can be displayed on the display, thus acquiring a sharp divided image with a reduced influence of weak fluorescence emitted from the background.

When the examination angle, for example, is varied, and accordingly the grayscale levels of the pixels in the divided image are varied by an error factor, the threshold-setting section can update the threshold with the variation in grayscale level, and the image-adjusting section can thereby maintain the sharpness of the divided image. Thus, quantitative information about the subject can be acquired.

That is, the second aspect allows highly quantitative fluorescence examination with precisely reduced angle dependence.

In the above aspects, the reference-light-image acquiring section may acquire reflected or scattered reference light reflected or scattered back from the subject.

With this configuration, because the reference-light image is generated from the reflected or scattered reference light reflected or scattered back from the subject, the grayscale levels of the reference-light image are not zero or near zero even in a region where almost no fluorescence occurs, thus allowing an accurate divided image to be generated.

In the above aspects, the light source may further irradiate the subject with white light, the image-adjusting section may generate a background-removed image in which the region with grayscale levels below the threshold is not displayed, the fluoroscopy apparatus may further include a white-light-image acquiring section that acquires a white-light image of the subject irradiated with the white light and an image-combining section that generates a combined image in which the white-light image acquired by the white-light-image acquiring section and the background-removed image generated by the image-adjusting section are superimposed, and the display may display the combined image generated by the image-combining section.

Because the image-combining section generates a combined image in which the white-light image acquired by the white-light-image acquiring section and the background-removed image generated by the image-adjusting section are superimposed, the positional relationship between the white-light image and the divided image can be more clearly presented to the operator. In this case, because the region below the threshold is not displayed, the divided image does not interfere with the display of the white-light image in the region other than the affected area in the combined image in which both images are superimposed.

In the above aspects, the light source may irradiate the subject with white light as the reference light, the reference-light-image acquiring section may acquire an image of white light returning from the subject as the reference-light image, the image-adjusting section may generate a background-removed image in which the region with grayscale levels below the threshold is not displayed, the fluoroscopy apparatus may further include an image-combining section that generates a combined image in which the white-light image of the subject acquired by the reference-light-image acquiring section and the background-removed image generated by the image-adjusting section are superimposed, and the display may display the combined image generated by the image-combining section.

With this configuration, because the white-light image generated from the light reflected from the subject and the light scattered back from the subject is used as the reference-light image, the grayscale levels of the reference-light image are not zero or near zero even in a region where almost no fluorescence occurs, thus allowing an accurate divided image to be generated.

Because the image-combining section generates a combined image in which the white-light image acquired by the white-light-image acquiring section and the background-removed image generated by the image-adjusting section are superimposed, the positional relationship between the white-light image and the divided image can be more clearly presented to the operator. In this case, because the region below the threshold is not displayed, the divided image does not interfere with the display of the white-light image in the region other than the affected area in the combined image in which both images are superimposed.

In the above aspects, the threshold-setting section may set the threshold based on the mean grayscale level and a standard deviation.

With this configuration, even if the grayscale levels of the pixels in the divided image vary, the threshold-setting section can set a more precise threshold than the threshold-setting section sets a threshold based only on the mean grayscale level.

The threshold-setting section may set a threshold obtained by adding the standard deviation to the mean grayscale level.

In the above aspects, the preprocessing section may normalize the fluorescence intensity of each pixel of the fluorescence image and the return-light intensity of each pixel of the reference-light image by gains and exposure times of the fluorescence-image capturing section and the reference-light-image capturing section to generate a normalized fluorescence image and a normalized reference-light image and may multiply at least one of the normalized fluorescence image and the normalized reference-light image by the coefficient to generate a correction fluorescence image and a correction reference-light image.

With this configuration, even if different gain adjustments or exposure time adjustments are performed in the fluorescence-image acquiring section and the reference-light-image acquiring section during the acquisition of the fluorescence image and the reference-light image, the preprocessing section normalizes them to generate a normalized fluorescence image and a normalized reference-light image and uses them to generate a correction fluorescence image and a correction reference-light image, thus allowing more highly quantitative fluorescence examination.

In the above aspects, the fluoroscopy apparatus may further include a storage section that stores the coefficient, and the preprocessing section may multiply at least one of the fluorescence image and the reference-light image by the coefficient stored in the storage section.

With this configuration, highly quantitative fluorescence examination with reduced distance or angle dependence can be performed simply by multiplying the coefficient stored in the storage section.

In the above aspects, the fluoroscopy apparatus may further include an attachable and detachable component that is attached and detached to change examination conditions, the attachable and detachable component may have identification information recorded therein, the fluoroscopy apparatus may further include an identification-information reading part for reading the identification information stored in the attachable and detachable component, and the storage section may store the coefficient in association with the identification information.

In this case, when the attachable and detachable component is attached and detached to change the examination conditions, the identification-information reading part reads the identification information stored in the attachable and detachable component, and the coefficient stored in the storage section in association with the identification information can be set. Examples of attachable and detachable components include scopes such as those of endoscope apparatuses, and examples of examination conditions that are changed in that case include the NA and pupil diameter of the objective optical system, the wavelength of the fluorescence that can be examined, and the examination target site (such as the stomach or the large intestine). This allows an optimum coefficient to be set depending on the examination conditions and thus allows highly quantitative fluorescence examination even if the examination conditions are varied.

A third aspect of the present invention is a fluoroscopy system including the fluoroscopy apparatus according to the first aspect; a calibration device that is connected to the fluoroscopy apparatus and that calculates the coefficient, the calibration device including the standard sample and an examination-distance setting mechanism that sets the examination distance of the fluoroscopy apparatus so as to be variable relative to the standard sample; and a coefficient-determining section that calculates a coefficient by which at least one of the fluorescence image and the reference-light image is multiplied so that the distance characteristics of fluorescence intensity and the distance characteristics of return-light intensity are directly proportional, based on the examination distance set by the examination-distance setting mechanism and a fluorescence image and a reference-light image acquired by capturing an image of the standard sample with the fluoroscopy apparatus.

According to the third aspect of the present invention, images of the standard sample can be captured with the fluoroscopy apparatus while changing the examination distance of the fluoroscopy apparatus relative to the standard sample with the examination-distance setting mechanism of the calibration device to obtain the distance characteristics of fluorescence intensity and the distance characteristics of return-light intensity of the standard sample, and coefficients by which both distance characteristics are made directly proportional can be calculated based on these distance characteristics. The calculated coefficients can be stored in the storage section of the fluoroscopy apparatus to perform fluorescence examination of a subject by the fluoroscopy apparatus using a precisely calculated coefficient irrespective of differences between individual fluoroscopy apparatuses and, if any attachable and detachable component is provided, differences between individual attachable and detachable components, thus allowing more highly quantitative fluorescence examination.

A fourth aspect of the present invention is a fluoroscopy system including the fluoroscopy apparatus according to the second aspect; a calibration device that is connected to the fluoroscopy apparatus and that calculates the coefficient, the calibration device including the standard sample and an examination-angle setting mechanism that sets the examination angle of the fluoroscopy apparatus so as to be variable relative to the standard sample; and a coefficient-determining section that calculates a coefficient by which at least one of the fluorescence image and the reference-light image is multiplied so that the angle characteristics of fluorescence intensity and the angle characteristics of return-light intensity are directly proportional, based on the examination angle set by the examination-angle setting mechanism and a fluorescence image and a reference-light image acquired by capturing an image of the standard sample with the fluoroscopy apparatus.

According to the fourth aspect of the present invention, images of the standard sample can be captured with the fluoroscopy apparatus while changing the examination angle of the fluoroscopy apparatus relative to the standard sample with the examination-angle setting mechanism of the calibration device to obtain the angle characteristics of fluorescence intensity and the angle characteristics of return-light intensity of the standard sample, and coefficients by which both angle characteristics are made directly proportional can be calculated based on these angle characteristics. The calculated coefficients can be stored in the storage section of the fluoroscopy apparatus to perform fluorescence examination of a subject by the fluoroscopy apparatus using a precisely calculated coefficient irrespective of differences between individual fluoroscopy apparatuses and, if any attachable and detachable component is provided, differences between individual attachable and detachable components, thus allowing more highly quantitative fluorescence examination.

A fifth aspect of the present invention is a fluorescence-image processing method using a fluorescence image acquired by capturing fluorescence emitted from a subject when the subject is irradiated with excitation light and a reference-light image acquired by capturing return light returning from the subject when the subject is irradiated with reference light. The method includes a preprocessing step of multiplying at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image; a divided-image generating step of dividing the correction fluorescence image generated by the preprocessing step by the correction reference-light image to generate a divided image; a threshold-setting step of setting a threshold based on a mean grayscale level of pixels in the divided image generated by the divided-image generating step; an image-adjusting step of enhancing contrast between a region with grayscale levels above the threshold set by the threshold-setting step and a region with grayscale levels below the threshold in the divided image; and a display step of displaying the divided image with the contrast enhanced by the image-adjusting step.

A sixth aspect of the present invention is a fluorescence-image processing method using a fluorescence image acquired by capturing fluorescence emitted from a subject when the subject is irradiated with excitation light and a reference-light image acquired by capturing return light returning from the subject when the subject is irradiated with reference light. The method includes a preprocessing step of multiplying at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image; a divided-image generating step of dividing the correction fluorescence image generated by the preprocessing step by the correction reference-light image to generate a divided image; a threshold-setting step of setting a threshold based on a mean grayscale level of pixels in the divided image generated by the divided-image generating step; an image-adjusting step of enhancing contrast between a region with grayscale levels above the threshold set by the threshold-setting step and a region with grayscale levels below the threshold in the divided image; and a display step of displaying the divided image with the contrast enhanced by the image-adjusting step.

The present invention provides the advantage of allowing examination with a highly quantitative fluorescence image by sufficiently removing the residual dependence on factors such as distance from a divided image.

REFERENCE SIGNS LIST 10 light source
41 reference-image generating section
42 fluorescence-image generating section
43 divided-image generating section
44 image-normalizing section
45 threshold-setting section
46 preprocessing section
47 image-combining section
48 white-light-image generating section
50 monitor (display)
51 image-adjusting section
60 IC chip
61 identification-information reading section (identification-information reading part)
62 storage section
70 fluoroscopy system
71 calibration device
72 coefficient-determining section
74 standard sample
75 linear-motion stage (examination-distance setting mechanism)
76 tilt stage (examination-angle setting mechanism)
100, 101, 102, 103 fluoroscopy apparatus

The invention claimed is:

1. A fluoroscopy apparatus comprising:
a light source that irradiates a subject with excitation light and reference light;
a fluorescence-image acquiring section that captures fluorescence emitted from the subject irradiated with the excitation light from the light source to acquire a fluorescence image;
a reference-light-image acquiring section that captures return light returning from the subject irradiated with the reference light from the light source to acquire a reference-light image;
a preprocessing section that multiplies at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image;
a divided-image generating section that divides the correction fluorescence image generated by the preprocessing section by the correction reference-light image to generate a divided image;
a threshold-setting section that sets a threshold based on a mean grayscale level of pixels in the divided image generated by the divided-image generating section;
an image-adjusting section that enhances contrast between a region with grayscale levels above the threshold set by the threshold-setting section and a region with grayscale levels below the threshold in the divided image; and
a display that displays the divided image with the contrast enhanced by the image-adjusting section.

2. The fluoroscopy apparatus according to claim 1, wherein the reference-light-image acquiring section acquires reflected or scattered reference light reflected or scattered back from the subject.

3. The fluoroscopy apparatus according to claim 1, wherein the light source further irradiates the subject with white light;
the image-adjusting section generates a background-removed image in which the region with grayscale levels below the threshold is not displayed;
the fluoroscopy apparatus further comprises
a white-light-image acquiring section that acquires a white-light image of the subject irradiated with the white light, and
an image-combining section that generates a combined image in which the white-light image acquired by the white-light-image acquiring section and the background-removed image generated by the image-adjusting section are superimposed; and
the display displays the combined image generated by the image-combining section.

4. The fluoroscopy apparatus according to claim 1, wherein the light source irradiates the subject with white light as the reference light;
the reference-light-image acquiring section acquires an image of white light returning from the subject as the reference-light image;
the image-adjusting section generates a background-removed image in which the region with grayscale levels below the threshold is not displayed;
the fluoroscopy apparatus further comprises an image-combining section that generates a combined image in which the white-light image of the subject acquired by the reference-light-image acquiring section and the background-removed image generated by the image-adjusting section are superimposed; and
the display displays the combined image generated by the image-combining section.

5. The fluoroscopy apparatus according to claim 1, wherein the threshold-setting section sets the threshold based on the mean grayscale level and a standard deviation.

6. The fluoroscopy apparatus according to claim 1, wherein the preprocessing section normalizes the fluorescence intensity of each pixel of the fluorescence image and the return-light intensity of each pixel of the reference-light image by gains and exposure times of the fluorescence-image acquiring section and the reference-light-image acquiring section to generate a normalized fluorescence image and a normalized reference-light image and multiplies at least one of the normalized fluorescence image and the normalized reference-light image by the coefficient to generate a correction fluorescence image and a correction reference-light image.

7. The fluoroscopy apparatus according to claim 1, wherein the fluoroscopy apparatus further comprises a storage section that stores the coefficient; and
the preprocessing section multiplies at least one of the fluorescence image and the reference-light image by the coefficient stored in the storage section.

8. The fluoroscopy apparatus according to claim 7, wherein the fluoroscopy apparatus further comprises an attachable and detachable component that is attached and detached to change examination conditions;
the attachable and detachable component has identification information recorded therein;
the fluoroscopy apparatus further comprises an identification-information reading part for reading the identification information stored in the attachable and detachable component; and
the storage section stores the coefficient in association with the identification information.

9. A fluoroscopy system comprising:
the fluoroscopy apparatus according to claim 1;
a calibration device that is connected to the fluoroscopy apparatus and that calculates the coefficient,
the calibration device including the standard sample and an examination-distance setting mechanism that sets the examination distance of the fluoroscopy apparatus so as to be variable relative to the standard sample; and
a coefficient-determining section that calculates a coefficient by which at least one of the fluorescence image and the reference-light image is multiplied so that the distance characteristics of fluorescence intensity and the distance characteristics of return-light intensity are directly proportional, based on the examination distance set by the examination-distance setting mechanism and the fluorescence image and the reference-light image acquired by capturing an image of the standard sample with the fluoroscopy apparatus.

10. A fluoroscopy apparatus comprising:
a light source that irradiates a subject with excitation light and reference light;
a fluorescence-image acquiring section that captures fluorescence emitted from the subject irradiated with the excitation light from the light source to acquire a fluorescence image;
a reference-light-image acquiring section that captures return light returning from the subject irradiated with the reference light from the light source to acquire a reference-light image;
a preprocessing section that multiplies at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image;
a divided-image generating section that divides the correction fluorescence image generated by the preprocessing section by the correction reference-light image to generate a divided image;
a threshold-setting section that sets a threshold based on a mean grayscale level of pixels in the divided image generated by the divided-image generating section;
an image-adjusting section that enhances contrast between a region with grayscale levels above the threshold set by the threshold-setting section and a region with grayscale levels below the threshold in the divided image; and
a display that displays the divided image with the contrast enhanced by the image-adjusting section.

11. A fluoroscopy system comprising:
the fluoroscopy apparatus according to claim 10;
a calibration device that is connected to the fluoroscopy apparatus and that calculates the coefficient,
the calibration device including the standard sample and an examination-angle setting mechanism that sets the examination angle of the fluoroscopy apparatus so as to be variable relative to the standard sample; and
a coefficient-determining section that calculates a coefficient by which at least one of the fluorescence image and the reference-light image is multiplied so that the angle characteristics of fluorescence intensity and the angle characteristics of return-light intensity are directly proportional, based on the examination angle set by the examination-angle setting mechanism and the fluorescence image and the reference-light image acquired by capturing an image of the standard sample with the fluoroscopy apparatus.

12. The fluoroscopy apparatus according to claim 10, wherein the reference-light-image acquiring section acquires reflected or scattered reference light reflected or scattered back from the subject.

13. The fluoroscopy apparatus according to claim 10, wherein
the light source further irradiates the subject with white light;
the image-adjusting section generates a background-removed image in which the region with grayscale levels below the threshold is not displayed;
the fluoroscopy apparatus further comprises a white-light-image acquiring section that acquires a white-light image of the subject irradiated with the white light, and
an image-combining section that generates a combined image in which the white-light image acquired by the white-light-image acquiring section and the background-removed image generated by the image-adjusting section are superimposed; and
the display displays the combined image generated by the image-combining section.

14. The fluoroscopy apparatus according to claim 10, wherein
the light source irradiates the subject with white light as the reference light;
the reference-light-image acquiring section acquires an image of white light returning from the subject as the reference-light image;
the image-adjusting section generates a background-removed image in which the region with grayscale levels below the threshold is not displayed;
the fluoroscopy apparatus further comprises an image-combining section that generates a combined image in which the white-light image of the subject acquired by the reference-light-image acquiring section and the background-removed image generated by the image-adjusting section are superimposed; and
the display displays the combined image generated by the image-combining section.

15. The fluoroscopy apparatus according to claim 10, wherein the threshold-setting section sets the threshold based on the mean grayscale level and a standard deviation.

16. The fluoroscopy apparatus according to claim 10, wherein the preprocessing section normalizes the fluorescence intensity of each pixel of the fluorescence image and the return-light intensity of each pixel of the reference-light image by gains and exposure times of the fluorescence-image acquiring section and the reference-light-image acquiring section to generate a normalized fluorescence image and a normalized reference-light image and multiplies at least one of the normalized fluorescence image and the normalized reference-light image by the coefficient to generate a correction fluorescence image and a correction reference-light image.

17. The fluoroscopy apparatus according to claim 10, wherein
the fluoroscopy apparatus further comprises a storage section that stores the coefficient; and
the preprocessing section multiplies at least one of the fluorescence image and the reference-light image by the coefficient stored in the storage section.

18. The fluoroscopy apparatus according to claim 17, wherein
the fluoroscopy apparatus further comprises an attachable and detachable component that is attached and detached to change examination conditions;
the attachable and detachable component has identification information recorded therein;
the fluoroscopy apparatus further comprises an identification-information reading part for reading the identification information stored in the attachable and detachable component; and
the storage section stores the coefficient in association with the identification information.

19. A fluorescence-image processing method using a fluorescence image acquired by capturing fluorescence emitted from a subject when the subject is irradiated with excitation light and a reference-light image acquired by capturing return light returning from the subject when the subject is irradiated with reference light, the method comprising:
a preprocessing step of multiplying at least one of the fluorescence image and the reference-light image by a coefficient by which distance characteristics of fluorescence intensity and distance characteristics of return-light intensity acquired from a standard sample in advance are made directly proportional to each other to generate a correction fluorescence image and a correction reference-light image;
a divided-image generating step of dividing the correction fluorescence image generated by the preprocessing step by the correction reference-light image to generate a divided image;
a threshold-setting step of setting a threshold based on a mean grayscale level of pixels in the divided image generated by the divided-image generating step;
an image-adjusting step of enhancing contrast between a region with grayscale levels above the threshold set by the threshold-setting step and a region with grayscale levels below the threshold in the divided image; and
a display step of displaying the divided image with the contrast enhanced by the image-adjusting step.

20. A fluorescence-image processing method using a fluorescence image acquired by capturing fluorescence emitted from a subject when the subject is irradiated with excitation light and a reference-light image acquired by capturing return light returning from the subject when the subject is irradiated with reference light, the method comprising:
a preprocessing step of multiplying at least one of the fluorescence image and the reference-light image by a coefficient by which angle characteristics of fluorescence intensity and angle characteristics of return-light intensity acquired from a standard sample in advance are made directly proportional to each other to generate a correction fluorescence image and a correction reference-light image;
a divided-image generating step of dividing the correction fluorescence image generated by the preprocessing step by the correction reference-light image to generate a divided image;
a threshold-setting step of setting a threshold based on a mean grayscale level of pixels in the divided image generated by the divided-image generating step;
an image-adjusting step of enhancing contrast between a region with grayscale levels above the threshold set by the threshold-setting step and a region with grayscale levels below the threshold in the divided image; and
a display step of displaying the divided image with the contrast enhanced by the image-adjusting step.

* * * * *